United States Patent [19]

Sugiura et al.

[11] Patent Number: 4,689,426

[45] Date of Patent: Aug. 25, 1987

[54] 5-ALKYLIDENE-2-HALO-4-SUBSTITUTED-2-CYCLOPENTENONE AND PROCESS FOR PRODUCTION THEREOF

[75] Inventors: Satoshi Sugiura; Toshio Tanaka; Seizi Kurozumi, all of Tokyo, Japan

[73] Assignee: Teijin Limited, Osaka, Japan

[21] Appl. No.: 628,107

[22] Filed: Jul. 5, 1984

[30] Foreign Application Priority Data

Jul. 6, 1983 [JP] Japan .............................. 57-121518
Oct. 27, 1983 [JP] Japan .............................. 57-199921

[51] Int. Cl.$^4$ ........................................... C07C 177/00
[52] U.S. Cl. ................................... 560/121; 556/441; 560/51; 560/53; 560/231; 562/459; 562/463; 562/503
[58] Field of Search ................... 560/121, 231, 51, 53; 562/503, 459, 463; 556/941

[56] References Cited

U.S. PATENT DOCUMENTS 3,755,426  8/1973  Strike .................................. 560/121

Primary Examiner—Robert Gerstl
Attorney, Agent, or Firm—Sughrue, Mion, Zinn, Macpeak and Seas

[57] ABSTRACT

Novel 5-alkylidene-2-halo-4-substituted-2-cyclopentenone and process for production thereof. The novel 5-alkylidene-2-halo-4-substituted-2-cyclopentenones are represented by the following formula (I):

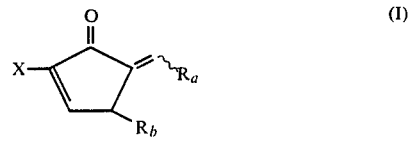

wherein $R_a$ represents a substituted or unsubstituted aliphatic hydrocarbon group having 1 to 12 carbon atoms or a substituted or unsubstituted phenyl group, $R_b$ represents a substituted or unsubstituted aliphatic hydrocarbon group having 1 to 12 carbon atoms, and X represents a halogen atom. The novel cyclopentenones possess excellent pharmaceutical activities including anti-tumor activity, antiviral activity and antimicrobial activity.

2 Claims, No Drawings

5-ALKYLIDENE-2-HALO-4-SUBSTITUTED-2-CYCLOPENTENONE AND PROCESS FOR PRODUCTION THEREOF

FIELD OF THE INVENTION

This invention relates to 5-alkylidene-2-halo-4-substituted-2-cyclopentenone compounds and a process for production thereof.

More specifically, this invention relates to novel 5-alkylidene-2-halo-4-substituted-2-cyclopentenone compounds having a structure similar to prostaglandin A or D which possess such excellent pharmacological activities as anti-tumor (anti-neoplastic) activity, antiviral activity, anti-microbial activity, etc., and a process for their production.

BACKGROUND OF THE INVENTION

Natural prostaglandins (hereinafter sometimes referred to as PG) are compounds which have singular biological activities including platelet aggregation inhibiting activity, blood pressure lowering activity, etc., and are useful natural substances which have recently been used as remedies for peripheral circulatory disorders in the medical field. Among prostaglandins, prostaglandins A are known as ones which have a double bond in their cyclopentenone ring and, for instance, prostaglandin A$_2$ is expected as the drug to display blood pressure lowering activity (E. J. Corey et al., *J. Amer. Chem.*, 95, 6831 (1973)).

It has been reported that prostaglandin A series have a realizable possibility of becoming antitumor agents in view of their strong action to inhibit the synthesis of DNA (*Biochem. Biophys. Res. Commun.* 87, 795 (1979); W. A. Turner et al., *Prostaglandins Relat. Lipids*, 2, 265–8 (1982)).

M. Fukushima et al. examined the effect of PGD$_2$ to inhibit proliferation of L1210 mouse leukemia cells and human leukemia cell lines, and reported the IC$_{50}$ of PGD$_2$ on L1210 cells is 2.4 micrograms/ml (*Biochem. Biophys. Res. Commun.*, 105, 956 (1982)).

On the other hand, U.S. Pat. No. 3,755,426 disclosed the 10-halogenated-derivatives of prostaglandins A which have broncho-dilator activity and blood pressure lowering activity, but this patent contains no disclosure concerning the possibility of their use as antitumor agents.

SUMMARY OF THE INVENTION

It is an object of this invention to provide novel 5-alkylidene-2-halo-4-substituted-2-cyclopentenones.

Another object of this invention is to provide novel 5-alkylidene-2-halo-4-substituted-2-cyclopentenones which have a 5-membered cyclic ring like prostaglandins of certain types.

Still another object of this invention is to provide novel 5-alkylidene-2-halo-4-substituted-2-cyclopentenones which have better antitumor activity than hitherto known prostaglandins.

Still another object of this invention is to provide novel 5-alkylidene-2-halo-4-substituted-2-cyclopentenones which have strong antiviral activity.

Still another object of this invention is to provide novel 5-alkylidene-2-halo-4-substituted-2-cyclopentenones which have strong antimicrobial activity.

Still another object of this invention is to provide novel 5-alkylidene-2-halo-4-substituted-2-cyclopentenones which show some selective antitumor activity as a biological activity and do not substantially show such anit-hypertensive activity or platelet aggregation inhibiting activity as exhibited by known PGA$_2$.

Still another object of this invention is to provide a very simple process for producing the 5-alkylidene-2-halo-4-substituted-2-cyclopentenones of this invention.

Further objects and advantages of this invention will become apparent from the following description.

In accordance with this invention, these objects and advantages are achieved by providing a 5-alkylidene-2-halo-4-substituted-2-cyclopentenone represented by the following formula (I):

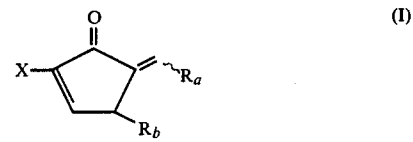

wherein R$_a$ represents a substituted or unsubstituted aliphatic hydrocarbon group having 1 to 12 carbon atoms or a substituted or unsubstituted phenyl group, R$_b$ represents a substituted or unsubstituted aliphatic hydrocarbon group having 1 to 12 carbon atoms, and X represents a halogen atom.

This invention also provides two processes for producing a 5-alkylidene-2-halo-4-substituted-2-cyclopentenone of the above formula (I).

One process comprises:

(a) halogenating and then dehydrating a 2,3-epoxy-cyclopentenone of the following formula (II):

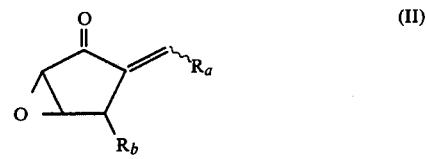

wherein R$_a$ and R$_b$ are as defined above, and (b) thereafter optionally removing a protecting group, hydrolyzing, or forming a salt of the compound of the formula (I).

The other process comprises:

(a) reacting a 2-hydrocarbon selenium-2-cyclopentenone represented by the following formula (III):

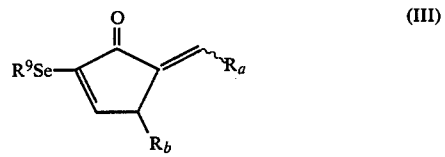

wherein R$^9$ represents an alkyl group having 1 to 4 carbon atoms or a substituted or unsubstituted aromatic hydrocarbon, and R$_a$ and R$_b$ are as defined above, with a hydrocarbon selenium halide represented by the following formula (IV):

wherein R$^{10}$ represents an alkyl group having 1 to 4 carbon atoms or a substituted or unsubstituted aromatic hydrocarbon, and X is as defined above, and (b) thereafter optionally removing a protecting group, hydrolyzing, or forming a salt of the compound of the formula (I).

DETAILED DESCRIPTION OF THE INVENTION

In formula (I), $R_a$ represents a substituted or unsubstituted aliphatic hydrocarbon group having 1 to 12 carbon atoms, or a substituted or unsubstituted phenyl group. $R_b$ represents a substituted or unsubstituted aliphatic hydrocarbon group having 1 to 12 carbon atoms.

The aliphatic hydrocarbon groups for Ra and Rb may be linear, branched or cyclic or may contain a carbon-carbon double or triple bond.

Preferably, the aliphatic hydrocarbon groups include, for example, linear or branched $C_{1-12}$ alkyl, alkenyl or alkynyl groups, and cycloalkyl groups having 3 to 8 carbon atoms.

Specific examples of alkyl groups having 1 to 12 carbon atoms are methyl, ethyl, n-propyl, isopropyl, n-butyl, sec-butyl, tert-butyl, n-pentyl, n-hexyl, n-heptyl, n-octyl, 3,7-dimethylactyl, n-nonyl, n-decyl, n-undecyl and n-dodecyl.

Specific examples of the alkenyl groups having 1 l to 12 carbon atoms are ethenyl, 1-propen-1-yl, 2-propen-1-yl, 1-buten-1-yl, 1,3-butadien-1-yl, 2-buten-1-yl, 1-penten-1-yl, 2-penten-1-yl, 1-hexen-1-yl, 2-hexen-1-yl, 1,5-hexadien-1-yl, 2,5-hexadien-1-yl, 3-hexen-1-yl, 1-hepten-1-yl, 1-octen-1-yl, 1,7-octadien-1-yl, 3,7-dimethyl-6-octen-1-yl, 1-nonen-1-yl, 1-decen-1-yl, 1-undecen-1-yl and 1-dodecen-1-yl.

Specific examples of the alkynyl groups having 1 to 12 carbon atoms are ethynyl, 1-propyn-1-yl, 2-propyn-1-yl, 1-butyn-1-yl, 3-buten-1yne-1-yl, 2-butyn-1-yl, 1-pentyn-1-yl, 2-pentyn-1-yl, 1-hexyn-1-yl, 2-hexyn-1-yl, 5-hexen-1-yne-1-yl, 3-hexen-1-yl, 1-heptyn-1-yl, 1-octyn-1-yl, 7-octen-1-yne-1-yl, 1-nonyn-1-yl, 1-decyn-1-yl, 1-undecyn-1-yl and 1-dodecyn-1-yl.

Examples of the cycloalkyl groups 3 to 8 carbon atoms are cyclopropyl, cyclopentyl, cyclohexyl, cyclooctyl and cyclohexenyl.

These aliphatic hydrocarbon groups or the phenyl group may have substituents.

Examples of the substituents include groups of the formula —COOR$^2$ (wherein R$^2$ represents a hydrogen atom, an alkyl group having 1 to 10 carbon atoms or one equivalent of a cation); groups of the formula —OR$^3$ (wherein R$^3$ represents a hydrogen atom, a $C_{1-6}$ alkyl group which may be substituted by a halogen atom, a $C_{1-7}$ carboacyl group, or a phenyl group which may be substituted by a halogen atom, an alkyl group having 1 to 4 carbon atoms which may be substituted by a halogen atom, or an alkoxy group having 1 t 4 carbon atoms); a phenyl group which may be substituted by a halogen atom, an alkyl group having 1 to 4 carbon atoms, or an alkoxy group having 1 to 4 carbon atoms which may be substituted by a carboacyl group having 1 to 7 carbon atoms; and cycloalkyl groups having 3 to 8 carbon atoms which may be substituted by an alkyl group having 1 to 4 carbon atoms; —CONR$^4$R$^5$ in which R$^4$ and R$^5$ respectively represent a hydrogen atom or an alkyl group having 1 to 6 carbon atoms; —COCH$_2$OH; or an oxo group.

Specific examples of the groups of the formula —COOR$^2$ are those in which R$^2$ is the same alkyl group as above having 1 to 10 carbon atoms, or one equivalent of a cation, for example an ammonium cation such as NH$_4$+, tetramethyl ammonium, monomethyl ammonium, dimethyl ammonium, trimethyl ammonium, benzyl ammonium, phenethyl ammonium, morpholinium cation, monoethanol ammonium or piperidinium cation, an alkali metal cation such as Na+, Li+ or K+, or a divalent or trivalent metal cation such as ½Ca$^{2+}$, ½Mg$^{2+}$, ½Zn$^{2+}$ or ⅓Al$^{3+}$.

Specific examples of the groups of the formula —OR$^3$ include a hydroxyl group; alkoxy groups having 1 to 6 carbon atoms such as methoxy, ethoxy, n-propoxy, isopropoxy, n-butoxy, n-pentyloxy and n-hexyloxy; carboacyloxy groups having 1 to 7 carbon atoms such as acetoxy, propionyloxy, n-butyryloxy, isobutyryloxy, n-valeryloxy, isovaleryloxy, caproyloxy, enanthyloxy and benzoyloxy; and a phenoxy group. The $C_{1-6}$ alkoxy groups for —OR$^3$ may be substituted by halogen atoms, thus providing chloromethoxy, dichloromethoxy, trifluoromethoxy, etc. The phenyl moiety of the phenoxy group for —OR$^3$ may be substituted by a halogen atom such as chloro, bromo or fluoro, an alkyl group having 1 to 4 carbon atoms which may be substituted by a halogen atom such as methyl, trifluoromethyl, ethyl, propyl or butyl, or an alkoxy group having 1 to 4 carbon atoms such as methoxy, ethoxy, propoxy or butoxy.

The phenyl group represented by $R_a$ or a substituent of $R_a$ or $R_b$ may be substituted by a halogen atom such as chloro, bromo and fluoro; an alkyl group having 1 to 4 carbon atoms such as methyl, ethyl, propyl and butyl; or an alkoxy group having 1 to 4 carbon atoms which may be substituted by a carboacyl group having 1 to 7 carbon atoms such as methoxy, ethoxy, propoxy and 1-methoxycarbonylethoxy.

The cycloalkyl group having 3 to 8 carbon atoms represented by $R_a$ or $R_b$ or a substituent of $R_a$ or $R_b$ may be substituted by an alkyl group having 1 to 4 carbon atoms, thus providing cyclopentyl, cyclohexyl, 3-methylcyclopentyl, 4-methylcyclohexyl, 3,3-dimethylcyclopentyl and 3-methylcyclopentyl.

Specific examples of the groups of the formula —CONR$^4$R$^5$ include aminocarbonyl, N,N-dimethylaminocarbonyl, N,N-diethyl-aminocarbonyl and N-methylaminocarbonyl.

In formula (I), X represents a halogen atom such as chloro, bromo and fluoro.

Among the 5-alkylidene-2-halo-4-substituted-2-cyclopentenones of the aforementioned formula (I), 5-alkylidene-2-halo-4-substituted-2-cyclopentenone of the following formula (I)-1 is preferred.

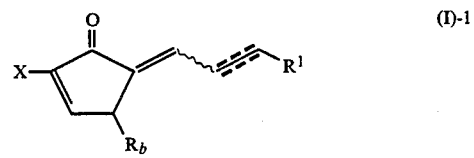

(I)-1 wherein R$^1$ represents a hydrogen atom, or a substituted or unsubstituted aliphatic hydrocarbon group having 1 to 10 carbon atoms, the symbol ⇜ represents a single, double or triple bond, and R$_b$ and X are the same as defined for formula (I).

R$^1$ in formula (I)-1 represent a hydrogen atom or an aliphatic hydrocarbon group having 1-10 carbon atoms. The aliphatic hydrocarbon group may be substituted.

The aliphatic hydrocarbon group having 1 to 10 carbon atoms may be linear, branched or cyclic, and may have a carbon-carbon double bond.

Examples of preferred aliphatic hydrocarbon groups having 1 to 10 carbon atoms include linear or branched alkyl or alkenyl groups and cycloalkyl groups having 3 to 8 carbon atoms.

Specific examples of the alkyl groups having 1 to 10 carbon atoms include methyl, ethyl, n-propyl, iso-propyl, n-butyl, sec-butyl, tert-butyl, n-pentyl, n-hexyl, n-heptyl, n-octyl, n-nonyl and n-decyl.

Specific examples of the alkenyl groups having 1 to 10 carbon atoms include ethenyl, 1-propeny-1-yl, 2-propen-1-yl, 3-buten-1-yl, 1-buten-1-yl, 4-penten-1-yl, 5-hexen-1-yl, 6-penten-1-yl, 7-octen-1-yl, 8-nonen-1-yl and 9-decen-1-yl. Of these, 1-propen-1-yl, 2-propen-1-yl, 3-buten-1-yl, 4-penten-1-yl and 5-hexen-1-yl are preferred.

Examples of the cycloalkyl groups having 3 to 8 carbon atoms are the same as those given for $R_a$ in formula (I).

Examples of the substituents of the aliphatic hydrocarbon group are the same as those given for $R_a$ or $R_b$ in formula (I).

In formula (I)-1, the symbol ⫽ represents a single, double or triple bond.

Among the compounds of formula (I)-1, A-type prostaglandins of the following formula (I)-2 and D-type prostaglandins of the following formula (I)-3 are especially preferred:

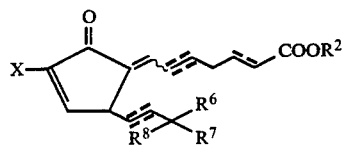
(I)-2 wherein $R^6$ represents a hydrogen atom or a methyl group, $R^7$ represents a hydrogen atom or a substituted or unsubstituted aliphatic hydrocarbon group having 1 to 9 carbon atoms, $R^8$ represents a hydrogen atom, a hydroxyl group or a protected hydroxyl group, the symbol ⑁ represents a single or double bond, and X, $R^2$ and the symbol ⫽ are the same as defined above;

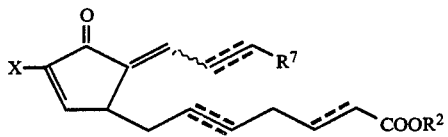
(I)-3 wherein $R^2$, $R^7$, X and the symbols ⫽ and ⑁ are the same as defined above.

$R^6$ in formula (I)-2 represents a hydrogen atom, or a methyl group.

$R^7$ in formula (I)-2 and (I)-3 represents a hydrogen atom or an aliphatic hydrocarbon group having 1 to 9 carbon atoms. The aliphatic hydrocarbon group may be substituted.

Examples of the aliphatic hydrocarbon group having 1 to 9 carbon atoms include linear or branched alkyl groups such as methyl, ethyl, n-propyl, isopropyl, n-butyl, sec-butyl, t-butyl, n-pentyl, n-hexyl, 2-methyl-1-hexyl, 2-methyl-2-hexyl, n-heptyl and n-octyl, and the same $C_{3-8}$ cycloalkyl groups as exemplified above.

The aliphatic hydrocarbon group may be substituted by a halogen atom; —$OR^3$; a phenyl group which may be substituted by a halogen atom, an alkyl group having 1 to 4 carbon atoms or an alkoxy group having 1 to 4 carbon atoms which may be substituted by a carboacyl group having 1 to 7 carbon atoms; or a cycloalkyl group having 3 to 8 carbon atoms which may be substituted by an alkyl group having 1 to 4 carbon atoms.

The specific representative examples of these substituents are the same as those described for $R_a$ in formula (I).

$R^8$ in formula (I)-2 represents a hydrogen atom, a hydroxyl group or a protected hydroxyl group. Examples of the protected group for the hydroxyl group are tri($C_{1-7}$ hydrocarbon) silyl groups and groups forming an acetal linkage with the oxygen atom of the hydroxyl group.

Specific examples of preferred tri($C_{1-7}$ hydrocarbon)-silyl groups include tri($C_{1-4}$ alkyl)-silyl groups such as trimethyl-silyl, triethylsilyl or t-butyldimethylsilyl, diphenyl($C_{1-4}$ alkyL)silyl groups such as t-butyldiphenylsilyl, and a tribenzylsilyl group.

Examples of the groups forming an acetal linkage together with the oxygen atom of the hydroxyl group include methoxymethyl, 1-ethoxyethyl, 2-methoxy-2-propyl, 2-ethoxy-2-propyl, (2-methoxyethoxy)methyl, benzyloxymethyl, 2-tetrahydropyranyl, 2-tetrahydrofuranyl and 6,6-dimethyl-3-oxa-2-oxo-bicyclo[3.1.0-]hex-r-yl groups. Of these, 2-tetrahydropyranyl, 2-tetrahydrofuranyl, 1-ethoxyethyl, 2-methoxy-2-propyl, (2-methoxyethoxy)methyl and 6,6-dimethyl-3-oxa-2-oxo-bicyclo[3.1.0]hex-4-yl groups are particularly preferred.

The symbol ⑁ in formulae (I)-2 and (I)-3 represents a single or double bond.

The symbol ⫽ in formulae (0-2 and (I)-3 represents a single, double or triple bond.

X in the formulae (I)-2 and (I)-3 is the same as in the formula (I).

The following examples are given for the novel 5-alkylidene-2-halo-4-substituted-2-cyclopentenone of the above formula (I), (including formulae (I)-1, (I)-2, and (I)-3.)

(i) Compounds of Formula (I)-2.

(100) 2-chloro-4-butyl-5-(6-carboxyhexylidene)-2-cyclo-pentenone, (102) 2-chloro-4-octyl-5-(6-carboxyhexylidene)-2-cyclopentenone, (104) 2-chloro-4-(1-octenyl)-5-(6-carboxyhexylidene)-2-cyclopentenone, (106) 2-chloro-4-(3-hydroxy-1-octenyl)-5-(6-carboxyhexylidene)-2-cyclopentenone, (108) 2-bromo-4-(3-hydroxy-3-cyclohexyl-1-propenyl)-5-(6-carboxyhexylidene)-2-cyclopentenone, (110) 2-chloro-4-(3-hydroxy-3-cyclopentyl-1-propenyl)-5-(6-carboxyhexylidene)-2-cyclopentenone, (112) 2-bromo-4-(2-propenyl)-5-(6-carboxyhexylidene)-2-cyclopentenone, (114) 2-chloro-4-(3-hydroxy-5-methyl-1-nonenyl)-5-(6-carboxyhexylidene)-2-cyclopentenone, (116) 2-chloro-4-(3-hydroxy-3-phenyl-1-propenyl)-5-(6-carboxyhexylidene)-2-cyclopentenone, (118) 2-chloro-4-(1-hydroxy-3-phenyl-1-propenyl)-5-(6-carboxyhexylidene)-2-cyclopentenone.

(120) 2-bromo-4-(3-hydroxy-3-methyl-1-propenyl)-5-(6-carboxyhexylidene)-2-cyclopentenone, (122) 2-bromo-4-(3-hydroxy-5,5-dimethyl-1-octenyl)-5-(6-carboxyhexylidene)-2-cyclopentenone, (124) 2-fluoro-4-(3-hydroxy-4-phenoxy-1-butenyl)-5-(6-carboxyhexylidene)-2-cyclopentenone, (126) 2-chloro-4-butyl-5-(6-carboxy-2-hexenylidene)-2-cyclopentenone, (128) 2-bromo-4-butyl-5-(6-carboxy-2-hexenylidene)-2-cyclopentenone,
(130) 2-chloro-4-butyl-5-(6-carboxy-5-hexenylidene)-2-cyclopentenone,
(132) 2-chloro-4-octenyl-5-(6-carboxy-2-hexenylidene)-2-cyclopentenone,
(134) 2-chloro-4-octenyl-5-(6-carboxy-2-hexenylidene)-2-cyclopentenone,
(136) 2-chloro-4-(3-hydroxy-1-octenyl)-5-(6-carboxy-2-hexynylidene)-2-cyclopentenone,
(138) 2-bromo-4-(3-hydroxy-3-cyclopentyl-1-propenyl)-5-(6-carboxy-2-hexenylidene)-2-cyclopentenone,
(140) 2-bromo-4-(3-hydroxy-3-cyclohexyl-1-propenyl)-5-(6-carboxy-2-hexynylidene)-2-cyclopentenone,
(142) 2-fluoro-4-butyl-5-(2-methylpropylidene)-2-cyclopentenone,
(144) 2-chloro-4-butyl-5-(2,2-dimethylpropylidene)-2-cyclopentenone,
(146) 2-chloro-4-(3-hydroxy-1-octenyl)-5-butylidene-2-cyclopentenone,
(148) 2-chloro-4-butyl-5-(3-phenyl-2-propenylidene)-2-cyclopentenone,
(150) 2-bromo-4-octyl-5-(2-methylpropylidene)-2-cyclopentenone,
(152) 2-chloro-4-(1-octenyl)-5-(6-carboxy-2-hexenylidene)-2-cyclopentenone,
(154) 2-fluoro-4-butyl-5-heptylidene-2-cyclopentenone,
(156) 2-chloro-4-octyl-5-heptylidene-2-cyclopentenone,
(158) 2-chloro-4-(3-hydroxy-1-octenyl)-5-heptylidene-2-cyclopentenone,
(160) 2-bromo-4-butyl-5-(7-hydroxyheptylidene)-2-cyclopentenone,
(162) 2-chloro-4-octyl-5-(7-hydroxyheptylidene)-2-cyclopentenone,
(164) 2-chloro-4-(3-hydroxy-1-octenyl)-5-(7-hydroxyheptylidene)-2-cyclopentenone,
(166) 2-bromo-4-(1-octenyl)-5-(7-hydroxyheptylidene)-2-cyclopentenone,
(168) 2-chloro-4-(3-hydroxy-4-m-fluorophenoxy)-5-(6-carboxyhexylidene)-2-cyclopentenone,
(170) 2-bromo-4-(3-hydroxy-4-m-trifluoromethylphenyl)-5-(6-carboxyhexylidene)-2-cyclopentenone,
(172) 2-fluoro-4-(1-octyne)-5-(6-carboxyhexylidene)-2-cyclopentenone,
(174) 2-chloro-4-(6-chloro-3,7-dimethyloctyl)-5-(6-methoxycarboxylhexylidene)-2-cyclopentenone,
(176) 2-chloro-4-(3,7-dimethyl-6-octene-1-yl)-5-(6-carboxyhexylidene)-2-cyclopentenone,
(178) 2-chloro-4-(3-hydroxy-1-octenyl)-5-[m-(methoxycarbonylethyloxy)phenyl methylidene]-2-cyclopentenone,
(180) 2-chloro-4-(1-octenyl)-5-(4-acetoxy-6-carboxy-2-hexenylidene)-2-cyclopentenone,
(182) 2-chloro-4-(3-hydroxy-1-octenyl)-5-(6-N,N-dimethylaminocarbonylhexylidene)-2-cyclopentenone,
(184) 2-chlor-4-(3-hydroxy-1-octenyl)-5-(6-N,N-diethylaminocarbonylhexylidene)-2-cyclopentenone.

(ii) Compounds of Formula (I)-3.
(200) 2-chloro-4-(6-carboxyhexyl)-5-[3-(3-propylcyclopentyl)-2-propenylidene]-2-cyclopentenone,
(202) 2-chloro-4-(6-carboxy-2-hexenyl)-5-[3-(3-propylcyclopentyl)-2-propenylidene]-2-cyclopentenone,
(204) 2-chloro-4-(6-carboxy-2,5-hexadienyl)-5-[3-(3-propylcyclopentyl)-2-propenylidene]-2-cyclopentenone,
(206) 2-chloro-4-(6-carboxyhexyl)-5-(2-octenylidene)-2-cyclopentenone,
(208) 2-chloro-4-(6-carboxyhexyl)-5-(3-phenoxy-2-propenylidene)-2-cyclopentenone,
(210) 2-chloro-4-(6-carboxyhexyl)-5-[3-(p-trifluoromethylphenoxy)-2-propenylidene]-2-cyclopentenone, (iii) Compounds of Formula (I), other than Formulae (I)-2 and (I)-3.
(300) 2-chloro-4-(2-octenyl)-5-(6-carboxyhexylidene)-2-cyclopentenone,
(302) 2-bromo-4-(2-octenyl)-5-(6-carboxyhexylidene)-2-cyclopentenone,
(304) 2-chloro-4-(2-octenyl)-5-(6-carboxy-2-hexenylidene)-2-cyclopentenone,
(306) 2-chloro-4-(2-octenyl)-5-(4-acetoxy-6-carboxy-2-hexenylidene)-2-cyclopentenone,
(308) 2-chloro-4-(3-octenyl)-5-(6-carboxyhexylidene)-2-cyclopentenone,
(310) 2-bromo-4-(2,6-octadienyl)-5-(6-carboxyhexylidene)-2-cyclopentenone.

The novel 5-alkylidene-2-halo-4-substituted-2-cyclopentenones of this invention can be produced according to the following Reaction Scheme A or B.

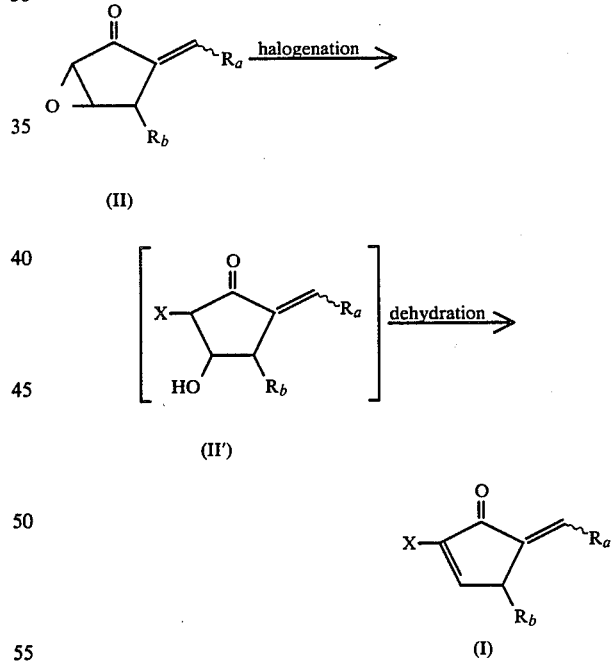

According to this invention, 5-alkylidene-2-halo-4-substituted-2-cyclopentenone of Formula (I) is produced by subjecting the 2,3-epoxycyclopentenone of Formula (II) to a halogenation reaction and dehydration reaction, and, if required, further subjecting the reaction production to a deprotecting, hydrolyzing or salt-forming reaction.

X, $R_a$ and $R_b$ in Formulae (II) and (II') are as defined with regard to Formula (I).

2,3-Epoxycyclopentenone of Formula (II) can be produced according to the reaction scheme shown below.

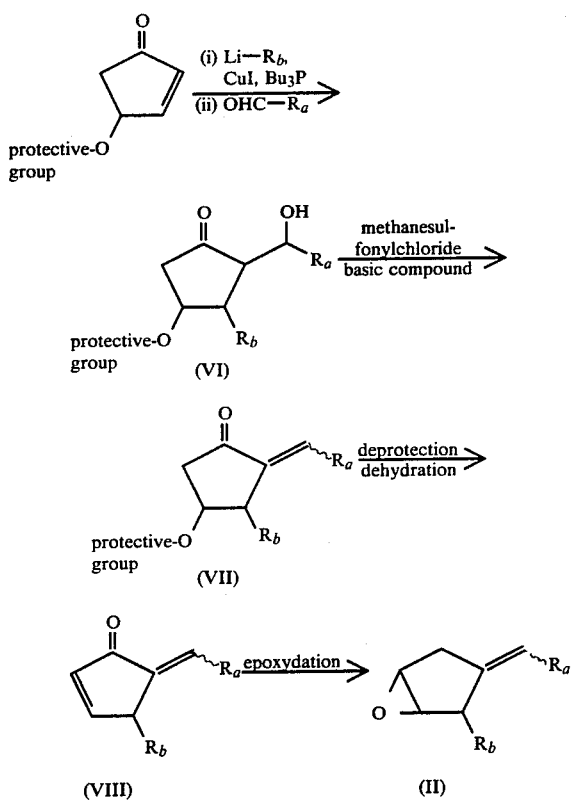

The process of conversion from the compound (V) to the compound (VII) is described in U.S. Pat. No. 4,315,032 (incorporated herein by reference) and also in European Laid-Open Patent Publication No. 0079733 (incorporated herein by reference). The conversion from the compound (VII) to the compound (VIII) is disclosed in U.S. patent application Ser. No. 534,256, and is described below. The compound (II) can be obtained by treating the compound (VII) with hydrogen peroxide in the present of a basic compound such as sodium hydroxide, etc. (U.S. Pat. No. 3,755,426 incorporated herein by reference).

The deprotection of the compound of the formula (VII) can be carried out as described below.

The dehydration reaction of the 5-alkylidene-3-hydroxy-4-substituted cyclopentenone of formula (VII) is preferably carried out in the presence of a dehydrating agent. Examples of the dehydrating agent include inorganic acids such as hydrochloric acid, hydrobromic acid, hydrofluoric acid and phosphoric acid, organic carboxylic acids such as propionic acid, oxalic acid, citric acid and maleic acid, and organic sulfonic acids such as methanesulfonic acid, ethanesulfonic acid, benzenesulfonic acid and p-toluenesulfonic acid. Of these, the inorganic acids and organic carboxylic acids are preferred. The amount of the dehydrating agent used is preferably 0.5 to 100 moles, especially preferably 1 to 50 moles, per mole of the 5-alkylidene-3-hydroxy-4-substituted cyclopentenone. As a reaction solvent, there may be used an ether such as tetrahydrofuran, dioxane, dimethoxyethane or diethyl ether, an alcohol such as methanol or ethanol, dimethyl sulfoxide, dimethylformamide, hexamethylphosphoric triamide, acetonitrile, and water, either singly or in combination with each other.

The reaction temperature is preferably 0° to 80° C., especially preferably 10° to 50° C.

The reaction time varies depending upon the starting compound, the dehydrating agent and the reaction solvent used in the reaction. Usually, it is 10 minutes to 10 days, preferably 20 minutes to 5 days. After the deprotection reaction, the dehydration reaction can be carried out in the same reaction mixture.

The compound (VIII) can also be produced according to a method in which the prostaglandin D-type compounds described in Prostaglandins, 9, 109 (1975); J. Org. Chem., 38, 2115 (1973); J. Chem. Soc., Chem. Commun., 156 (1979); or Tetrahedron Lett., 2235 (1974) are subjected to a conventional dehydration reaction.

The compound (V) is well known and readily available to those of ordinary skill in the art.

In the process of this invention, 2,3-epoxycyclopentenone of formula (II) first undergoes a halogenation reaction.

Examples of the reagents to be used in the halogenation reaction include hydrohalogenic acids such as hydroiodic acid, hydrobromic acid, and hydrochloric acid; and metal halides such as titanium tetrachloride, tin tetrachloride, aluminum trichloride, iron trichloride, zinc chloride, titanium tetrabromide, and aluminum tribromide. Of the hydrohalogenic acids, hydroiodic acid, hydrobromic acid, and hydrochloric acid are preferred. Of the metal halides, tetrachloride, tin tetrachloride, and aluminum trichloride are preferred. Hydrobromic acid, hydrochloric acid and titanium tetrachloride are especially preferred.

In cases where the reagent to be used in the halogenation reaction are hydrohalogenic acids, the amount of hydrohalogenic acid is 1 to 100 moles, preferably 5 to 50 moles, per mole of 2,3-epoxycyclopentenone of formula (II).

As a reaction solvent, for use with the hydrohalogenic acids, solvents which are completely miscible with water can be used. Examples of suitable solvents include alcohols such as methanol, ethanol, and t-butyl alcohol; ketones such as acetone and methyl ethyl ketone; and ethers such as dioxane, tetrahydrofuran and dimethoxyethane. Among these solvents mentioned above, acetone, methyl ethyl ketone, methanol, ethonol, and t-butyl alcohol are used desirably and acetone and methanol are especially desirable.

In cases where the reagents to be used in the halogenation reaction are metal halides, the amount of metal halides is 1 to 200 moles, desirably 2 to 5 moles, in terms of halogen ion arising from the metal halogenide, per 1 mole of 2,3-epoxycyclopentenone of the aforementioned formula (II).

As a reaction solvent for use with the metal halides, halogenated hydrocarbons such as dichloromethane, chloroform, carbon tetrachloride, and tetrachloroethane; aromatic hydrocarbons such as benzene and toluene; saturated hydrocarbons such as hexane and cyclohexane; and alcohols such as methanol and ethanol may be mentioned. Of these solvents, halogenated hydrocarbons such as dichloromethane, chloroform, carbon tetrachloride, and tetrachloroethane are desirably used.

The reaction temperature for halogenation should desirably be in the range of −40°–50° C., especially desirably in the range of −5° to 30° C.

The reaction time for halogenation varies depending upon the material compounds, reagents, reaction solvents, and reaction temperature; however, it is usually in the range of 5 minutes to 5 hours, desirably 10 minutes to 1 hour.

Upon the termination of the halogenation reaction, a 2-halo-3-hydroxy-cyclopentenone expressed by the formula (II') is formed. This compound may be separated and purified according to the usual procedures such as extraction, washing with water, drying, chromatography, etc. However, it is a usual practice when hydrohalogenic acids are used to halogenate, to subject the reaction mixture to the dehydration reaction as mentioned below without isolating said 2-halo-3-hydroxy-cyclopentenone.

As the dehydrating agents to be used in the dehydration reaction of the 2-halo-hydroxycyclopentenone of formula (II') which is an intermediate obtained in the abovementioned reaction, there are inorganic acids such as hydrochloric acid, hydrobromic acid, hydrofluoric acid, and phosphonic acid; organic carboxylic acids such as acetic acid, propionic acid, oxalic acid, citric acid, and malic acid; and organic sulfonic acids such as methanesulfonic acid, ethanesulfonic acid, benzenesulfonic acid, and p-toluenesulfonic acid. The reaction is desirably carried out in the presence of an inorganic acid or organic carboxylic acid selected from among those mentioned above.

In cases where hydrohalogenic acids such as hydroiodic acid, hydrochloric acid and hydrobromic acid are used in the aforementioned halogenation reaction, the dehydration reaction can be carried out in the same reaction system in succession to the halogenation reactions.

The amount of a dehydrating agent to be used in the reaction should desirably be 0.5 to 100 moles, more desirably 1 to 50 moles, per mole of the intermediate 2-halo-3-hydroxy-cyclopentenone of formula (II').

As the solvents for the dehydraftion reaction, when dehydrating the isolated compound (II'), ethers such as tetrahydrofuran, dioxane, and dimethoxyethane; alcohols such as methanol, ethanol, and t-butyl alcohol; ketones such as acetone and methyl ethyl ketone; dimethyl sulfoxide, dimethylformamide, hexamethyl phosphoric triamide, acetonitrile and water can be used singly or in any combination thereof.

If the dehydration reaction is carried out in the same reaction system as the halogenation reaction, the solvents for the halogenation action are suitable.

The temperature of the dehydration reaction should desirably be in the range of 0° to 100° C., more desirably in the range of 10° to 80° C.

The time of the dehydration reaction varies depending upon the material compounds, dehydrating agents, and reaction solvents to be used; however, the reaction is usually carried out in the range of 10 minutes to 10 days, desirably 20 minutes to 5 days.

After the dehydration reaction is completed, 2-halo-2cyclopentenone expressed by the aforementioned formula (II) can be separated and purified according to the usual known procedures such as extraction, washing with water, drying, chromatography, etc.

When the resulting final compound has a group removable by hydrolysis or deprotection or a group capable of forming a salt by a salt-forming reaction, it is possible to subject the final compound to a hydrolysis, deprotection or salt-forming reaction.

Groups capable of being removed by hydrolysis are, for example, carboacyl groups or ester groups. The carboacyl groups can be hydrolyzed, for example, in an aqueous solution of sodium hydroxide, potassium hydroxide or calcium hydroxide, a water-alcohol mixture, a methanol or ethanol solution containing sodium methoxide, potassium methoxide or sodium ethoxide, The ester groups can be hydrolyzed, for example, in water or a solvent containing water at a temperature of −10° C. to +60° C. for a period of about 10 minutes to about 24 hours using an enzyme such as lipase.

Groups capable of being removed by deprotection are, for example, groups forming an acetal linkage with the oxygen atom of the hydroxyl group, or tri($C_{1-7}$ hydrocarbon)silyl groups. The removal of the protective group can be performed suitably, for example, by using acetic acid, a pyridinium salt of p-toluene-sulfonic acid, a cation exchange resin, etc., as a catalyst and water, tetrahydrofuran, diethyl ether, dioxane, acetone, acetonitrile, etc., as a reaction solvent when the protective group is a group forming an acetal linkage together with the oxygen atom of the hydroxyl group. The reaction is usually carried out at a temperature of −78° C. to +30° C. for about 10 minutes to about 3 days. When the protective group is a tri($C_{1-7}$ hydrocarbon)silyl group, the deprotecting reaction may be carried out in the presence of acetic acid, tetrabutyl ammonium fluoride, cesium fluoride, etc., in the same reaction solvent as cited above at the same temperature and for the same period of time as mentioned above.

When the final compound has a carboxyl group in the molecule, it can then optionally be subjected to a salt-forming reaction to obtain the final compound as a carboxylate salt. The salt-forming reaction is commonly known, and is carried out by neutralizing the carboxylic acid with a nearly equivalent of a basic compound such as sodium hydroxide, potassium hydroxide or sodium carbonate, or ammonia, trimethylamine, monoethanolamine or morpholine in a customary manner. The final desired compound can be isolated and purified, for example, by silica gel column chromatography, silica gel thin-layer chromatography, high performance liquid chromatography, Florisil column chromatography, etc.

Reaction Scheme B

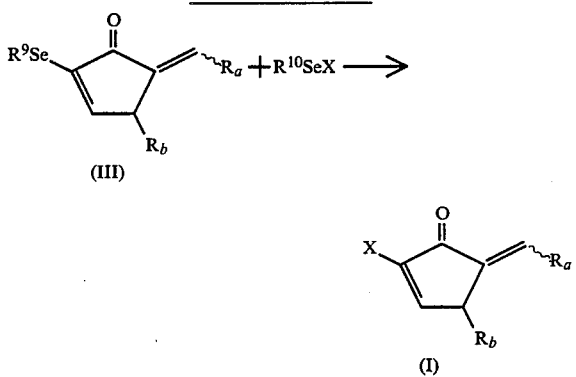

According to this invention, the 5-alkylidene-2-halo-4-substituted-2-cyclopentenone of Formula (I) is also produced by allowing 2-hydrocarbonselenium-2-cyclopentenone (III) to react with a hydrocarbonselenium halide (IV) and, if required, further subjecting the reaction product to a deprotecting, hydrolyzing or self-forming reaction.

$R_a$ and $R_b$ in Formula (III) are as defined above. $R^9$ in Formula (III) represents an alkyl group having 1 to 4 carbon atoms or aromatic hydrocarbon which may be substituted. Examples of the alkyl group having 1 to 4 carbon atoms are methyl, ethyl, n-propyl, isopropyl and butyl. Examples of the aromatic hydrocarbon are phenyl, 1-naphthyl and 2-naphthyl. The aromatic hydrocarbon may be substituted by a halogen atom such as chloro, bromo and fluoro; an alkyl group having 1 to 4 carbon atoms such as methyl, ethyl, n-propyl and n-butyl; and alkoxy group having 1 to 4 carbon atoms such as methoxy, ethoxy, propoxy and butoxy; or nitro group.

$R^{10}$ in Formula (IV) represents an alkyl group having 1 to 4 carbon atoms or aromatic hydrocarbon which may be substituted. Examples of $R^{10}$ are the same as those given for $R^9$ in Formula (III).

X in Formula (IV) represents a halogen atom such as chloro, bromo and fluoro.

The compound of Formula (III) can be produced according to the following reaction scheme.

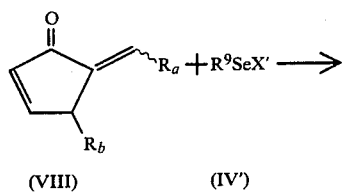

(VIII)    (IV')

(III)

The material compound of Formula (III) can be obtained by allowing the compound of Formula (VIII) to react with hydrocarbon selenium halide of Formula (IV'). The compound of Formula (VIII) can be obtained according to the method described in Reaction Scheme A. X' in Formula (IV') is a halogen atom such as chloro, bromo and fluoro. Examples of hydrocarbon selenium halide of Formula (IV') are the same as those of hydrocarbon selenium halides of Formula (IV), including, for instance, phenyl selenium chloride, m-trifluoromethylphenyl selenium chloride, o-nitrophenyl selenium chloride, p-chlorophenyl selenium chloride, o-trifluoromethyl-p-nitrophenyl selenium chloride, phenyl selenium bromide, p-methoxyphenyl selenium bromide, p-nitroselenium bromide, etc. Of these mentioned above, phenyl selenium chloride and phenyl selenium bromide are especially desirable.

Stoichiometrically, equimolecular amounts of hydrocarbon selenium halide of said Formula (IV') and 2-cyclopentenone of said Formula (VIII) are made to reaction with each other in the process; however, it is desirable to use 0.8 to 100 moles, and especially desirable to use 1 to 20 moles, of the former per mole of the latter in the actual reaction. It is desirable to carry out the reaction in the presence of a basic compound. As the basic compounds, carbonates such as sodium carbonate and potassium carbonate; bicarbonates such as sodium hydrogencarbonate and potassium hydrogencarbonate; aliphatic amines such as methylamine, dimethyl amine, ethylamine, diethylamine, triethylamine, dibutylamine, dusopropylamine, triisopropylamine, methylhexylamine, decylamine, dodecylamine, cyclopentylamine, dicyclohexylamine, benzylamine, dibenzylamine, α-phenethylamine, β-phenethylamine, ethylenediamine, and diethylenetriamine; and cyclic amines such as piperidine, morpholine, pyrrolidine, 1,4-diazabicyclo (2.2.2) octane, pyridine, butidine, collidine, and 4-N,N-dimethylaminopyridine are used.

The amount of a basic compound to be used should desirably be 1 to 500 moles, especially desirably 1 to 50 moles, per mole of said hydrocarbon selenium halide of Formula (IV').

As the reaction solvents, the aforementioned amines; aromatic hydrocarbons such as benzene and toluene; aliphatic hydrocarbons such as hexane, pentane, petroleum ether, and cyclohexane; ethers such as ether, tetrahydrofuran, and dimethoxyethane; halogenated hydrocarbons such as carbon tetrachloride, chloroform, dichloromethane, dichloroethane, and tetrachloroethane, and aprotic polar solvents such as dimethyl sulfoxide, dimethylformamide, and hexamethyl phosphoric triamide are used singly or in any combination thereof.

It is desirable to keep the reaction temperature in the range of −20° to 100° C., more desirably 0° to 50° C.

The reaction time varies depending upon the material compound, reagents, and reaction solvents; however, the reaction is usually carried out in the range of 5 minutes to 3 days, desirably in the range of 10 minutes to 1 day.

After the reaction is completed, 2-hydrocarbon selenium-2-cyclopentenone expressed by the aforementioned Formula (IV) which is used as a material compound in Reaction Scheme B may be separated and purified according to usual procedures such as extraction, washing with water, drying, chromatography, etc.; however, the reaction mixture can be directly subjected to Reaction Scheme B without isolating said 2-hydrocarbon selenium-2-cyclopentenone therefrom.

Stoichiometrically, in the Reaction Scheme B, hydrocarbon selenium halide of formula (IV) is reacted with 2-hydrocarbon selenium-2-cyclopentenone of Formula (III) obtained in the above reaction in equimolecular amounts; however, in actual reactions, it is desirable to use 0.8 to 100 moles, especially desirable 1 to 20 moles, of hydrocarbon selenium halide per mole of 2-hydrocarbon selenium-2-cyclopentenone. The reaction should desirably be conducted in the presence of a basic compound. Typical of such basic compounds include carbonates such as sodium carbonate and potassium carbonate; bicarbonates such as sodium hydrogencarbonate and potassium hydrogencarbonate; aliphatic amines such as methyl amine, dimethyl amine, ethylamine, diethylamine, triethylamine, dibutylamine, dusopropylamine, triisopropylamine, methyl hexylamine, decylamine, dodecylamine, cyclopentylamine, dicyclopentylamine, benzylamine, dibenzylamine, α-phenetylamine, β-phenetylamine, ethylendiamine, and diethylene-triamine; and cyclic amines such as piperidine, morpholine, pyrrolidine, 1,4-diazabicyclo (2.2.2) octane, pyridine, butidine, collidine, and 4-N,N-dimethylaminopyridine. Among these basic compounds, the cyclic amines such as pyridine, butidine, 4-N,N-dimethylaminopyridine, etc., are desirably used.

The desirable amount of basic compounds to be used is 1 to 500 moles, more desirably 1 to 50 moles, per mole of hydrocarbon selenium halide expressed by the aforementioned Formula (IV).

Typical of reaction solvents are the aforementioned amines; aromatic hydrocarbons such as benzene and toluene; aliphatic hydrocarbons such as hexane, pentane, petroleum ether and cyclohexane; ethers such as ether, tetrahydrofuran, and dimethoxyethane; halogenated hydrocarbons such as carbon tetrachloride, chloroform, dichloromethane, dichloroethane, and tetrachloroethane, and aprotic polar solvents such as dimethyl sulfoxide, dimethylformamide, and hexamethyl phosphoric triamide and they are used singly or in a proper combination thereof.

The reaction temperature should desirably be in the range of $-20°$ to $150°$ C., more desirably $0°$ to $100°$ C.

The reaction time varies depending upon the material compounds, reagents, and reaction solvents; however, the reaction is usually carried out in the range of 30 minutes to 10 days, desirably in the range of 1 hour to 5 days.

As seen from the above description, the reaction of 2-hydrocarbon selenium-2-cyclopentenone of Formula (III) with hydrocarbon selenium halide of Formula (IV) is conducted under almost the same conditions as the reaction of 2-cyclopentenone of Formula (VIII) with hydrocarbon selenium halide of Formula (IV'). Therefore, it is possible to first allow 2-cyclopentenone of Formula (VIII) to react with hydrocarbon selenium halide of Formula (IV') to obtain 2-hydrocarbon selenium-2-cyclopentenone, which is then made to successively react with hydrocarbon selenium halide of Formula (IV) in the same reaction system.

After the reaction terminates, the desired compound can be separated and purified according to commonly known procedures such as extraction, washing with water, drying, chromatography, etc.

If necessary, the desired compound may further be subjected to a hydrolyzing, deprotecting, or salt-forming reaction. Such a hydrolyzing, deprotecting, or salt-forming reaction can be carried out according to the same methods as mentioned hereinbefore.

The novel 5-alkylidene-2-halo-4-substituted-2-cyclopentenone compounds of the present invention have a strong anti-tumor (anti-neoplastic) activity and also an excellent anti-viral activity and antimicrobial activity and, therefore, they are very useful compounds as pharmaceuticals.

According to this invention, the 5-alkylidene-2-halo-4-substituted-2-cyclopentenone compounds can be administered orally, or parenterally through intrarectal, subcutaneous, intramuscular and intravenous routes, for example. For oral administration, the compounds of this invention may be formulated into solid or liquid preparations. Examples of the solid preparations are tablets, pills, powders and granules. In these solid preparations, at least one of the compounds of the present invention is mixed with sodium bicarbonate, calcium carbonate, potato starch, sucrose, mannitol, carboxymethyl cellulose, etc. These preparations can be formed in accordance with customary operations. The solid preparations may also include a lubricant, a sweetener, a stabilizer, an antiseptic, etc., such as calcium stearate, magnesium stearate or glycerol.

Examples of the liquid preparations for oral administration are emulsions, solutions, suspensions, syrups, and elixirs. The liquid preparations may further include a wetting agent, a suspending aid, a sweetener, a flavor, an aroma, a stabilizer, etc. The liquid preparations may be filled in capsules made of an absorbable material such as gelatin.

For intrarectal administration, ordinary suppositories such as soft gelatin capsules are used.

Examples of preparations for parenteral administration through other routes are preparations for subcutaneous, intramuscular or intravenous injection in the form of aseptic aqueous or non-aqueous solutions, suspensions and emulsions. The non-aqueous solutions and suspensions may include propylene glycol, polyethylene glycol, olive oil or injectable organic esters such as ethyl oleate. Such preparations may also contain an antiseptic, an emulsifier, a dispersant, a stabilizer, etc. These injectable preparations can be made aseptic by filtration through a bacteria-holding filter, blending of a germicide, or irradiation.

The dose of the compound of this invention differs depending upon the condition, age, sex and body weight of a subject to which it is to be administered, the route of administration, etc. Usually, it can be administered in a dose of about 1 $\mu$g to 100 mg/kg-body weight/day. The dose may be a single dose, or may be divided into several portions, for example 2 to 6 portions.

The pharmaceutical composition of this invention is preferably used as a medicament in unit dosage form.

By way of illustration, but not by way of limitation, the following examples are given to illustrate the practice of this invention.

EXAMPLE 1

Synthesis of 2-chloro-4-(1-octenyl)-5-(6-methoxycarbonylhexylidene)-2-cyclopentenone (i) 3.1 g (6.4 mmol) of 4-(1-octenyl)-5-(1-hydroxy-6-methoxy-carbonylhexyl)-3-(t-butyl-dimethylsilyloxy)-cyclopentenone was dissolved in 40 ml of dichloromethane, and 3.92 g (32.1 mmol) of dimethylaminopyridine was added. With ice cooling and stirring, 1.0 ml (12.9 mmol) of methanesulfonyl chloride was added. The mixture was stirred at 0° C. for 5 minutes, and then at room temperature for 12 hours. Furthermore, 0.78 g (6.4 mmol) of dimethylaminopyridine was added, and the mixture was stirred for 100 minutes. The mixture was poured into 20 ml of 0.5N hydrochloric acid and washed. The aqueous layer was extracted with dichloromethane. The collected organic layer was washed first with a saturated aqueous solution of sodium bicarbonate and then with a saturated aqueous solution of sodium chloride, and dried over anhydrous sodium sulfate. The dried product was filtered, concentrated and subjected to silica gel column chromatography (silica gel 150 g; eluent, hexane:ethyl acetate=20:1→7:1) to give 1.83 g (yield 61%) of 4-(1-octenyl)-5-(6-methoxycarbonylhexylidene)-3-(t-butyl-dimethylsilyloxy)-cyclopentenone. The spectral data of this compound were as follows:

TLC: Rf=0.45 (hexane:ethyl acetate=5:1).

NMR (CDCl$_3$)$\delta$: 0–0.2 (m, 6H), 0.83 (s, 9H), 0.7–1.1 (m, 3H), 1.0–2.8 (m, 22H), 3.1–3.4 (m, 1H), 3.59 (s, 3H), 3.9–4.3 (m, 1H), 5.1–5.5 (m, 2H), 6.61 (td, 1H, J=7.5, 2.0 Hz).

(ii) 1.3 g (2.8 mmol) of 4-(1-octenyl-5-(6-methoxycarbonyl-hexylidene)-3-(t-butyldimethylsilyloxy)cyclopentenone was dissolved in 40 ml of a mixed solvent consisting of acetic acid, tetrahydrofuran and water in a ratio of 2:1:1, and the solution was stirred at 60° C. for 15 hours. Toluene was added, and the mixture was concentrated under reduced pressure. A saturated aqueous solution of sodium bicarbonate was added. The mixture was extracted with ethyl acetate three times.

The organic layers were combined, washed with a saturated aqueous solution of sodium chloride and dried over anhydrous magnesium sulfate. The dried product was filtered, concentrated and subjected to silica gel column chromatography (silica gel 60 g; eluent, hexane:ethyl acetate=7:1→1:1) to give 635 mg (yield 70%) of 4-(1-octenyl)-5-(6-methoxycarbonylhexylidene)-2-cyclopentenone.

TLC: Rf=0.25 (hexane:ethyl acetate=5:1).

NMR (CDCl$_3$)δ: 0.85 (brt, 3H, J=4.2 Hz), 1.0–2.5 (m, 20H), 3.58 (s, 3HO), 3.7–4.1 (m, 1H), 5.12 (dd, 1H, J=15.0, 7.7 Hz), 5.52 (dt, 1H, J=15.0, 6.2 Hz), 6.19 (dd, 1H, J=5.8, 1.0 Hz), 6.49 (brt, 1H, J=7.8 Hz), 7.24 (dd, 1H, J=6.2, 2.2 Hz).

(iii) 2.0 g (6.0 mmol) of 4-(1-octenyl)-5-(6-methoxycarbonyl-hexylidene)-2-cyclopentenone was dissolved in 6 ml of methanol and 3.06 ml (30.0 mmol) of 30% aqueous hydrogen peroxide was added thereto with ice cooling and stirring. 200 microliter (200 micromol) of 1N sodium hydroxide was further added and the mixture was stirred at 0° C. for 20 minutes. A saturated aqueous solution of ammonium chloride was added and the mixture was extracted with hexane. The organic layer was washed with a saturated aqueous solution of sodium chloride, dried over magnesium sulfate, filtrated, concentrated, and subjected to chromatography on a column of silica gel (silica gel, 100 g; eluent, hexane:ethyl acetate=10:1→8:1) to give 1.63 g (yield 78%) of 2,3-epoxy-4-(1-octenyl)-5-(6-methoxy-carbonylhexylidene)cyclopentenone. The spectral data of this compound were as follows:

TLC; Rf=0.50 (eluent, hexane:ethyl acetate=2:1).

IR (liquid film): 1732, 1648, 840 cm$^{-1}$.

NMR (CDCl$_3$)δ: 0.84 (3H, brt, J=4.6 Hz), 1.0–1.8 (14H, m), 1.7–2.5 (6H, m), 3.3–3.5 (1H, m), 3.57(3H, s), 3.5–3.8 (2H, m), 5.15 (1H, dd, J=14.4, 7.0 Hz), 5.47 (1H, dt, J=14.4, 5.8 Hz), 6.57 (1H, td, J=7.2, 2.0 Hz).

(iv) 1.61 g (4.6 mmol) of 2,3-epoxy-4-(1-octenyl)-5-(6-methoxycarbonylhexylidene)cyclopentenone obtained in the preceding (iii) was dissolved in 15 ml of acetone, to which 3 ml of concentrated hydrochloric acid and the mixture was stirred for 1.5 hours. An aqueous solution (2N) of sodium hydroxide was added thereto and the mixture was extracted with ethyl acetate after adjustment of pH to pHG. The organic layer was washed with a saturated saline solution and dried over magnesium sulfate anhydride. After the reaction product was filtrated and concentrated, it was put to chromatography on a column of silica gel (silica gel, 80 g; eluent, cyclohexane:ethyl acetate=20:1–7:1) to obtain 107 mg (yield 6% of a low polar isomer (Z-form) of 2-chloro-4-(1-octenyl)-5-(6-methoxycarbonylhexylidene)-2-cyclopentenone and 1024 mg (yield 60%) of its high polar isomer (E-form).

Less polar isomer (Z-form).

TLC: Rf=0.57 (eluent; hexane:ethyl acetate=2:1).

IR (liquid film): 1738, 1699, 1647, 1587 cm$^{-1}$.

NMR (CDCl$_3$)δ: 0.84 (3H, brt, J=4.8 Hz), 1.0–2.5 (18H, m), 2.5–3.1 (2H, m), 3.58 (3H, s), 3.5–3.9 (1H, m), 5.08 (1H, dd, J=14.8, 7.8 Hz), 5.52 (1H, dt, J=14.8, 6.1 Hz), 5.98 (1H, brt, J=7.6 Hz), 7.07 (1H, d, 2.4 Hz).

More polar isomer (E-form).

TLC; Rf=0.51 (eluent, hexane:ethyl acetate=2.1).

IR (liquid film): 1738, 1710, 1657, 1586 cm$^{-1}$.

NMR (CDCl$_3$)δ: 0.84 (3H, brt, J=4.5 Hz), 1.0–2.5 (20H, m), 3.58 (3H, s), 3.7–4.1 (1H, m), 5.11 (1H, dd, J=15.2, 8.0 Hz), 5.56 (1H, dt, J-15.2, 6.2 Hz), 6.62 (1H, brt, J=7.0 Hz), 7.11 (1H, d, J=2.8 Hz).

EXAMPLE 2

Synthesis of 2-chloro-4-(1-octenyl)-5-(6-methoxycarbonylhexylidene)-2-cyclopentenone (i) 100 mg (0.3 mmol) of 2,3-epoxy-4-(1-octenyl)-5-(6-methoxycarbonylhexylidene)cyclopentenone obtained in Example 1, (iii), was dissolved in 2 ml of dichloromethane. 0.5 ml of a dichloromethane solution of 8% titanium tetrachloride was added to the solution and the mixture was stirred for 30 minutes. The reaction product thus obtained was washed with a saturated saline solution three times and then dried over sodium sulfate anhydride, followed by filtration and concentration to give an oily product mainly consisting of 2-chloro-3-hydroxy-4-(1-octenyl)-5-(6-methoxycarbonylhexylidene)cyclopentenone.

The obtained crude 2-chloro-3-hydroxy-4-(1-octenyl)-5-(6-methoxycarbonylhexylidene)cyclopentenone had the following spectral data.

TLC; Rf=1.45 and 0.38 (eluent; hexane;ethyl acetate=2:1).

IR (liquid film): 3470, 1736, 1644 cm$^{-1}$.

NMR (CDCl$_3$)δ: 0.84 (3H, brt, J=4.5 Hz), 1.0–1.8 (14H, m), 1.8–2.6 (7H, m), 3.0–3.5 (1H, m), 3.58 (3H, s), 3.7–4.6 (m, 2H), 5.1–5.8 (2H, m), 6.5–7.0 (m, 1H).

(ii) The oily product, which contained 2-chloro-3-hydroxy-4-(1-octenyl)-5-(6-methoxycarbonylhexylidene)cyclopentenone, obtained in the preceding (i) was dissolved in a mixed solvent consisting of 1 ml of acetic acid, 0.5 ml of tetrahydrofuran, and 0.5 ml of water and the solution was stirred at 80° C. for 4 hours. A saturated saline solution was added thereto and the mixture was extracted with ethyl acetate. Thereafter, the organic layer was washed first with a saturated aqueous solution of sodium hydrogencarbonate and then with a saturated saline solution. The reaction product was dried over magnesium sulfate anhydride, filtered, concentrated, and chromatographed on a column of silica gel (silica gel, 10 g; eluent, cyclohexane:ethyl acetate=15:1) to obtain 8 mg (yield 8%) of a less polar isomer (Z-form) of 2-chloro-4-(1-octenyl)-5-(6-methoxycarbonylhexylidene)-2-cyclopentenone as obtained in Example 1, (iv), and 56 mg (yield 53%) of its more polar isomer (E-form).

EXAMPLE 3

Synthesis of 2-bromo-4-(1-octenyl)-5-(6-methoxycarbonylhexylidene)-2-cyclopentenone (i) 100 mg (0.29 mmol) of 2,3-epoxy-4-(1-octenyl)-5-(6-methoxycarbonylhexylidene)cyclopentenone obtained in Example 1 (iii), was dissolved in 2 ml of acetone, 0.4 ml of 47% hydrobromic acid was added to the solution with ice cooling and stirring and the stirring was continued at 0° C. for 10 minutes. A saturated aqueous solution of sodium hydrogencarbonate was added thereto and the mixture was extracted with ethyl acetate and the organic layer was washed with a saturated saline solution, dried over magnesium sulfate anhydride, filtrated, and concentrated to give 122 mg of an oily reaction product mainly consisting of 2-bromo-3-hydroxy-4-(1-octenyl)-5-(6-methoxycarbonylhexylidene)cyclopentenone.

The spectral data of the thus obtained 2-bromo-3-hydroxy-4-(1-octenyl)-5-(6-methoxycarbonylhexylidene)cyclopentenone were as follows:

TLC; Rf=0.35 and 0.25 (eluent; hexane:ethyl acetate=3:1).

IR (liquid film): 3460, 1726, 1640 cm$^{-1}$.

NMR (CDCl$_3$)δ: 0.84 (3H, brt, J= 4.3 Hz), 1.0–1.8 (14H, m), 1.8–2.5 (6H, m), 2.5–3.4 (2H, m), 3.54 (3H, s), 3.8–4.4 (2H, m), 5.0–5.8 (2H, m), 6.71 (1H, td, J=7.5, 3.2 Hz).

(ii) 30 mg of the oily product, which mainly consisted of 2-bromo-3-hydroxy-4-(1-octenyl)-5-(6-methoxycarbonylhexylidene)cyclopentenone, obtained in the preceding (i) was dissolved in a mixed solvent comprising 1 ml of acetic acid, 0.5 ml of tetrahydrofuran, and 0.5 ml of water, and the solution was stirred at 70° C. for 3 hours. The reaction solution was poured over a saturated aqueous solution of sodium hydrogencarbonate and the mixture was extracted with hexane. The organic layer was washed with a saturated saline solution, dried over sodium sulfate anhydride, filtered, concentrated, and subjected to column chromatography on silica gel (silica gel, 15 g; eluent, cyclohexane:ethyl acetate=20.1→10:1) to obtain 13 mg (yield 44%) of 2-bromo-4-(1-octenyl)-5-(6-methoxycarbonylhexylidene)-2-cyclopentenone.

The spectral data of the thus obtained 2-bromo-4-(1-octenyl)-5-(6-methoxycarbonylhexylidene)-2-cyclopentenone were as follows:

TLC; Rf=0.52 (eluent, hexane:ethyl acetate=3:1).

IR (liquid film): 1738, 1713, 1658, 1578 cm$^{-1}$.

NMR (CDCl$_3$)δ: 0.83 (3H, brt, J=4.7 Hz), 1.0–2.5 (20H, m), 3.55 (3H, s), 3.6–4.0 (1H, m), 5.04 (1H, dd, J=15.2, 7.8 Hz), 5.51 (1H, dt, J=15.2, 6.2 Hz), 6.56 (1H, brt, J=7.2 Hz), 7.23 (1H, d, J=3.0 Hz).

EXAMPLE 4

Synthesis of 2-chloro-4-butyl-5-(6-methoxycarbonylhexylidene-2-cyclopentenone 660 mg (2.37 mmol) of 4-butyl-5-(6-methoxycarbonylhexylidene)-2-cyclopentenone was dissolved in 10 ml of methanol. With ice cooling and stirring, 1.2 ml of 30% aqueous hydrogen peroxide and then 0.23 ml of 1N sodium hydride were added to the solution and the mixture was stirred at 0° C. for 20 minutes. Saturated aqueous ammonium chloride was added thereto and was extracted with hexane. The organic layer was washed with a saturated saline solution, dried over sodium sulfate anhydride, filtered, concentrated, and chromatographed on a column of silica gel (silica gel, 30 g; eluent, hexane:ethyl acetate=10:1) to obtain 500 mg (yield 72%) of 2,3-epoxy-4-butyl-5-(6-methoxycarbonylhexylidene)cyclopentenone.

The spectral data of this compound were as follows:

TLC; Rf=0.40 (eluent, hexane:ethyl acetate=3:1).

IR (liquid film): 1735, 1651, 839 cm$^{-1}$.

NMR (CDCl$_3$)δ: 0.85 (3H, brt, J=5.0 Hz), 1.0–1.8 (12H, m), 1.8–2.5 (4H, m), 2.8–3.3 (1H, m), 3.34 (1H, d, J=2.8 Hz), 3.54 (3H, s), 3.64 (1H, d, J=2.8 Hz), 6.44 (1H, td, J=7.2, 2.0 Hz).

(ii) 300 mg (1.02 mmol) of 2,3-epoxy-4-butyl-5-(6-methoxycarbonylhexylidene)cyclopentenone was dissolved in 3 ml of acetone. 0.5 ml of concentrated hydrochloric acid was added to the solution and the mixture was stirred for 50 minutes. A saturated aqueous solution of sodium hydrogen carbonate was added thereto and was extracted with hexane. The organic layer was washed with a saturated saline solution, dried over sodium sulfate anhydride, filtrated, and subjected to column chromatography on silica gel (silica gel, 20 g; eluent, cyclohexane:ethyl acetate=10:1) to obtain 28 mg (yield 9%) of a less polar isomer (Z-form) of 2-chloro-4-butyl-5-(6-methoxycarbonyl-hexylidene)-2-cyclopentenone and 183 mg (yield 57%) of its more polar isomer (E-form).

The spectral data were as follows:

Less polar isomer (Z-form):

TLC; Rf=0.53 (eluent; benzene:ethyl acetate=10:1).

IR (liquid film): 1738, 1698, 1645, 1588 cm$^{-1}$.

NMR (CDCl$_3$)δ: 0.87 (3H, brt, J=4.7 Hz), 1.1–2.0 (12H, m), 2.0–2.5 (2H, m), 2.5–3.1 (2H, m), 3.1–3.5 (1H, m), 3.63 (3H, s), 6.13 (1H, brt, J=7.8 Hz), 7.33 (1H, d, J=3.5 Hz).

More polar isomer (E-form):

TLC; Rf=0.47 (eluent, benzene:ethyl acetate=10:1).

IR (liquid film): 1738, 1710, 1658, 1588 cm$^{-1}$.

NMR (CDCl$_3$)δ: 0.87 (3H, brt, J= 4.8 Hz), 1.1–1.95 (12H, m), 1.95–2.5 (4H, m), 3.3–3.8 (1H, m), 3.63 (3H, s), 6.64 (1H, brt, J=7.7 Hz), 7.41 (1H, d, J=2.6 Hz).

EXAMPLE 5

Synthesis of 2-bromo-4-butyl-5-(6-methoxycarbonylhexylidene)-2-cyclopentenone 100 mg (0.34 mmol) of 2,3-epoxy-4-butyl-5-(6-methoxycarbonylhexylidene)cyclopenenone obtained in Example 4, (i), was dissolved in 1 ml of acetone, to which 0.2 ml of hydrobromic acid was added, and the mixture was stirred for 1 hour. A saturated aqueous solution of sodium hydrogencarbonate was added thereto and extracted with hexane. The collected organic layer was washed with a saturated saline solution, dried over sodium sulfate anhydride, filtered, concentrated, and subjected to column chromatography on silica gel (silica gel, 10 g; eluent, cyclohexane:ethyl acetate=10:1) to give 3.5 mg (yield 3%) of a less polar isomer (Z-form) of 2-bromo-4-butyl-5-(6-methoxycarbonylhexylidene)-2-cyclopentenone and 43 mg (yield 35%) of its more polar isomer (E-form). The spectral data were as follows:

Less polar isomer (Z-form):

TLC; Rf=0.57 (eluent; benzyne:ethyl acetate=10:1).

IR (liquid film): 1736, 1698, 1642, 1580 cm$^{-1}$.

NMR (CDCl$_3$)δ: 0.88 (3H, brt, J=4.7 Hz), 1.1–2.0 (12H, m), 2.1–3.1 (4H, m), 3.4–3.9 (1H, m), 3.66 (3H, s), 6.14 (1H, t), 7.45–7.7 (1H, m), More polar isomer (E-form):

TLC; Rf=0.45 (eluent, benzene:ethyl acetate=10:1).

IR (liquid film): 1736, 1708, 1655, 1577 cm$^{-1}$.

NMR (CDCl$_3$)δ: 0.87 (3H, brt, J=4.7 Hz), 1.1–2.0 (12H, m), 2.0–2.6 (4H, m), 3.3–3.8 (1H, m), 3.66 (3H, s), 6.69 (1H, brt, J=7.1 Hz), 7.65 (1H, brd, J=3.2 Hz).

EXAMPLE 6

Synthesis of 2-chloro-4-butyl-5-(6-methoxycarbonylhexylidene)-2-cyclopentenone (i) 100 mg (0.36 mmol) of 4-butyl-5-(6-methoxycarbonylhexylidene)-2-cyclopentenone was dissolved in 3 ml of dichloromethane. After 49 μl of pyridine was added to the solution, 103 mg (0.54 mmol) of phenyl selenium chloride was further added thereto and the mixture was stirred for 4 hours. The reaction product was washed with 1N hydrochloric acid, then with a saturated aqueous solution of sodium hydrogencarbonate, and further with a saturated saline solution. The reaction product was then dried over sodium sulfate anhydride, filtrated, concentrated, and chromatographed on a column of silica gel (silica gel 40 g; eluent, cyclohexane:ethyl acetate=5:1) to obtain 140 mg (yield 90%) of 2-phenyl selenium-4-butyl-5-(6-methoxycarbonylhexylidene)-2-cyclopentenone. The spectral data of this compound were as follows:

TLC; Rf=0.58 (eluent, benzene:ethyl acetate=4:1).
IR (liquid film): 1738, 1692, 1651, 1562 cm$^{-1}$.
NMR (CDCl$_3$)δ: 0.82 (brt, 3H, J=5.3 Hz), 0.9–1.9 (m, 12H), 1.9–2.6 (m, 4H), 3.1–3.8 (m, 1H), 3.60 (s, 3H), 6.53 (brt, 1H, J=7.5 Hz), 6.88 (d, 1H, J=2.8 Hz), 7.0–7.8 (m, 4H).

(ii) 50 mg (0.12 mmol) of 2-phenyl selium-4-butyl-5-(6-methoxycarbonylhexylidene)-2-cyclopentenone obtained in the preceding (i) was dissolved in 2 ml of dichloromethane. 47 μl (0.58 mmol) of pyridine was first added to the solution and then 77 mg (0.40 mmol) of phenyl selenium chloride was added, and the mixture was refluxed for 20 hours.

The reaction product was first with 1N hydrochloric acid, then with a saturated aqueous solution of sodium hydrogen-carbonate, and finally with a saturated saline solution. The product was dried over sodium sulfate anhydride, filtered, concentrated, and subjected to column chromatography on silica gel (silica gel 20 g; eluent, cyclohexane:ethyl acetate=10:1→5:1) to obtain 7 mg (yield 18%) of a less polar isomer (Z-form) of 2-chloro-4-butyl-5-(6-methoxycarbonylhexylidene)-2-cyclopentenone and 24 mg of its more polar isomer (E-form).

The spectral data of these compounds were the same as that obtained in Example 4.

EXAMPLE 7

Synthesis of 2-chloro-4-butyl-5-(6-carboxyhexylidene)-2-cyclopentenone 20 ml of phosphate buffer (pH8) was added to a solution of 200 mg (0.64 mmol) of 2-chloro-4-butyl-5-(6-methoxycarbonylhexylidene)-2-cyclopentenone in 15 ml of acetone, and then 0.4 ml of an aqueous solution of pig liver esterase was added. The mixture was stirred at 30° C. for 60 hours. 1N hydrochloric acid was added to the reaction mixture to adjust the pH to 4, and then the mixture was saturated with ammonium sulfate. It was filtered, and then extracted with ethyl acetate. The organic layer was washed with a saturated aqueous solution of sodium chloride, and dried over anhydrous magnesium sulfate. The dried product was filtered, concentrated and subjected to silica gel column chromatography (silica gel, 10 g; eluent, hexane:ethyl acetate=3:2) to give 75 mg (yield 39%) of 2-chloro-4-butyl-5-(6-carboxyhexylidene)-2-cyclopentenone.

IR (liquid film): 3500–2600, 1708, 1658, 1585 cm$^{-1}$.
NMR (CDCl$_3$)δ: 0.87 (3H, brt, J=5.4 Hz), 1.0–2.7 (16H, m), 3.3–3.7 (1H, m), 6.69 (1H, brt, J=7.4 Hz), 7.44 (1H, d, J=2.8 Hz), 9.0–9.8 (1H, m).

EXAMPLE 8

Synthesis of 2-chloro-4-octyl-(6-methoxycarbonylhexylidene)-2-cyclopentenone 17 mg (51 mmol) of 4-octyl-5-(6-methoxycarbonylhexylidene)-2-cyclopentenone was dissolved in 1 ml of dichloromethane and 23 μl (280 μmol) of pyridine was added thereto. With stirring, 49 mg (254 mmol) of phenyl selenium chloride was added to the mixture and the reaction mixture was refluxed. 10 hours later, 23 μl (280 mmol) of pyridine and 49 mg (254 mmol) of phenyl selenium chloride were further added and the mixture was refluxed for 25 hours. 0.5 ml of pyridine was added to the reaction mixture and then, with vigorous stirring, 35% aqueous hydrogen, peroxide was further added and the mixture was stirred for another 1 hour. Hydrochloric acid and water were added thereto for extraction and the aqueous layer was then extracted twice with dichloromethane. The organic layer was washed first with a saturated aqueous solution of sodium hydrogencarbonate and then with a saturated saline solution and dried over sodium sulfate anhydride. Thereafter, it was filtered, concentrated, and chromatographed on a column of silica gel (silica gel 5 g; eluent, hexane:ethyl acetate=30:1→10:1) to obtain 10 mg (yield 53%) of 2-chloro-4-octyl-5-(6-methoxycarbonylhexylidene)-2-cyclopentenone.

The spectral data of this compound were as follows:
TLC; Rf=0.42 (eluent, benzene:ethyl acetate=10:1).
IR (liquid film): 1738, 1710, 1658, 1587 cm$^{-1}$.
NMR (CDCl$_3$)δ: 0.86 (brt, 3H, J=4.0 Hz), 1.1–2.0 (m, 20H), 2.0–2.6 (m, 4H), 3.2–3.8 (m, 1H), 3.67 (s, 3H), 6.68 (brt, 1H, J=8.2 Hz), 7.44 (d, 1H, J=2.4 Hz).

EXAMPLE 9

Synthesis of 10-chloro-7,8-dehydro PGA$_1$ methyl ester (i) 420 mg (1.21 mmol) of 7,8-dehydro PGA$_1$ methyl ester was dissolved in 10 ml of methanol. With ice cooling and stirring, 0.6 ml (6 mmol) of 30% aqueous hydrogen peroxide was first added to the solution and then 0.12 ml (0.12 mmol) of 1N aqueous sodium hydroxide was added thereto. After the mixture was stirred at 0° C. for 50 minutes, saturated aqueous ammonium chloride was added to the reaction mixture. The reaction mixture was extracted with ether, and the organic layer was washed with a saturated saline solution, dried over anhydrous magnesium sulfate, filtrated, concentrated, and subjected to silica gel column chromatography (silica gel, 15 g; eluent, hexane:ethyl acetate=5:1→2:1) to obtain 300 mg (yield 68%) of 10,11-epoxy-7,8-dehydro PGA$_1$ methyl ester.

Its spectral data were as follows:
TLC; Rf=0.41 (eluent, hexane:ethyl acetate=1:1)
IR (liquid film): 3460, 1727, 1646, 839 cm$^{-1}$.
NMR (CDCl$_3$)δ: 0.84 (3H, brt, J=4.4 Hz), 1.0–1.8 (14H, m), 1.8–2.5 (5H, m), 3.39 (1H, d, J=2.4 Hz), 3.55 (3H, s), 3.64 (1H, d, J=2.4 Hz), 3.5–3.8 (1H, m), 3.8–4.2 (1H, m), 5.3–5.7 (2H, m), 6.56 (1H, brt, J=7.0 Hz).

(ii) 300 mg of 10,11-epoxy-7,8-dehydro PGA$_1$ methyl ester obtained in the preceding (i) was dissolved in 3 ml of acetone and 0.6 ml of concentrated hydrochloric acid was added to the solution. The mixture was stirred for 45 minutes. A saturated aqueous solution of sodium hydrogencarbonate was added thereto and extracted with ethyl acetate. The organic layer was washed with a saturated saline solution, dried over anhydrous magnesium sulfate, filtrated, concentrated, and chromatographed on a column of silica gel (silica gel, 15 g; eluent, hexane:ethyl acetate=5:1→2:1) to obtain 143 mg (yield 45%) of 10-chloro-7,8-dehydro PGA$_1$ methyl ester.

The spectral data of the thus obtained 10-chloro-7,8-dehydro PGA$_1$ methyl ester were as follows:
TLC; Rf=0.20 (eluent, hexane:ethyl methyl=3:1)
IR (liquid film): 3450, 1735, 1709, 1655, 1584 cm$^{-1}$.

NMR (CDCl$_3$)δ: 0.86 (3H, brt, J= 5.6 Hz), 1.0–2.0 (14H, m), 2.0–2.6 (5H, m), 3.66 (3H, s), 3.8–4.3 (2H, m), 5.1–6.1 (2H m), 6.78 (1H, t, J=7.9 Hz), 7.1–7.4 (1H, m).

EXAMPLE 10

Synthesis of 2-chloro-4-(3,7-dimethyl-6-octenyl)-5-(6-methoxycarbonylhexylidene)-2-cyclopentenone; 2-chloro-4-(6-chloro-3,7-dimethyloctyl)-5-(6-methoxycarbonylhexylidene)-2-cyclopentenone; and 2-chloro-4-(6-chloro-3,7-dimethyloctyl)-5-(6-carboxylhexylidene)-2-cyclopentenone 422 mg (1.17 mmol) of 4-(3,7-dimethyl-6-octen-1-yl)-5-(6-methoxycarbonylhexylidene)-2-cyclopentenone was dissolved in 4 ml of methanol. With ice cooling and stirring, 600 μl (5.85 mmol) of 30% aqueous hydrogen peroxide and further 40 μl (40 mmol) of an aqueous solution of 1N sodium hydroxide were added thereto. After the mixture was stirred at 0° C. for 45 minutes, a saturated aqueous solution of ammonium chloride was added to the reaction mixture, the mixture was extracted with hexane, dried over anhydrous sodium sulfate, filtrated, and concentrated. 408 mg of the thus obtained oily product was dissolved in 4 ml of acetone. With ice cooling and stirring, 800 μm of concentrated hydrochloric acid was added to the solution and the mixture was stirred at 0° C. for 10 minutes and then at room temperature for 2 hours. A saturated saline solution was added thereto and the pH of the mixture was adjusted to 4 with an aqueous solution of 5N sodium hydroxide and extracted with ethyl acetate. The collected organic layer was washed with a saturated saline solution, dried over anhydrous sodium sulfate, filtered, concentrated, and subjected to silica gel column chromatography (silica gel, 45 g; eluent, cyclohexane:ethyl acetate=30:1→1:2) to obtain 28 mg (yield 6%) of a low polar isomer (Z-form) of 2-chloro-4-(3,7-dimethyl-6-octenyl)-5-(6-methoxycarbonylhexylidene)-2-cyclopentenone, 168 mg (yield 36%) of its high polyer isomer (E-form), 46 mg (yield 9%) of 2-chloro-4-)6-chloro-3,7-dimethyloctyl)-5-(6-methoxycarbonylhexylidene)-2-cyclopentenone, and 34 mg (yield 8%) of 2-chloro-4-(3,7-dimethyl-6-octenyl)-5-(6-carboxyhexylidene)-2-cyclopentenone.

The spectral data of 2-chloro-4-(3,7-dimethyl-6-octenyl)-5-(6-methoxycarbonylhexylidene)-2-cyclopentenone (Z-form) were as follows:

TLC; Rf=0.56 (eluent, hexane:ethyl acetate=3:1).
IR (liquid film): 1740, 1702, 1648, 1590 cm$^{-1}$.
NMR (CDCl$_3$)δ: 0.86 (3H, brd, J=4.2 Hz), 1.0–2.5 (23H, m), 2.5–3.05 (2H, m), 3.05–3.5 (1H, m), 3.65 (3H, 5), 5.09 (1H, brt, J=6.8 Hz), 6.17 (1H, t, J=8.0 Hz), 7.37 (1H, d, J=2.8 Hz).

The spectral data of 2-chloro-4-(3,7-dimethyl-6-octenyl)-5-(6-methoxycarbonylhexylidene)-2-cyclopentenone (E-form) were as follows:

TLC: Rf=0.50 (eluent, hexane:ethyl acetate=3.1).
IR (liquid film): 1741, 1714, 1660, 1588 cm$^{-1}$.
NMR (CDCl$_3$)δ: 0.85 (3H, brd, J=4.3 Hz), 1.0–2.5 (25H, m), 3.3–3.7 (1H, m), 3.66 (3H, s), 5.09 (1H, brt, J=6.6 Hz), 6.70 (1H, t, J=7.6 Hz), 7.45 (1H, d, J=2.8 Hz).

The spectral data of 2-chloro-4-(3,7-dimethyl-6-octenyl)-5-(6-carboxyhexylidene)-2-cyclopentenone (E-form) were as follows:

TLC: Rf=0.33 (eluent, hexane:ethyl acetate=1:3).
IR (liquid film): 3000, 1710, 1658, 1588 cm$^{-1}$.
NMR (CDCl$_3$)δ: 0.84 (3H, brd, J=4.2 Hz), 1.0–2.6 (25H, m), 3.3–3.7 (1H, m), 5.07 (1H, brt, J=7.0 Hz), 6.70 (1H, brt, J=7.6 Hz), 7.44 (1H, d, J=2.4 Hz), 8.9–9.8 (11H, m).

The spectral data of 2-chloro-4-(6-chloro-3,7-dimethyl-octyl)-5-(6-carboxylhexylidene)-2-chloropentenone were as follows:

TLC: Rf=0.41 (eluent, hexane:ethyl acetate=3:1).
IR (liquid film): 1739, 1711, 1657 1584 cm$^{-1}$.
NMR (CDCl$_3$)δ: 0.85 (3H, brd, J=4.2 Hz), 1.0–2.5 (19H, m), 1.53 (6H, s), 3.25–3.70 (1H, m), 3.65 (3H, s), 6.69 (1H, brt, J=7.9 Hz), 7.44 (1H, d, J=2.5 Hz).

EXAMPLE 11

Synthesis of 4(S)-2-chloro-4-(1-octenyl)-5-(6-methoxycarbonyl-hexylidene)-2-cyclopentenone (i) 140 microliters (1.2 mmol) of 30% aqueous hydrogen peroxide and 6 microliters of 1N aqueous sodium hydroxide were added to 80 mg (0.24 mmol) of (4S)-4-(1-octenyl)-5-(6-methoxy-carbonylhexylidene)-2-cyclopentenone in 2 ml of methanol. The mixture was stirred for 5 hours. The reaction mixture was neutralized by a saturated aqueous solution of ammonium chloride and then extracted with ether. The organic layer was washed, dried, concentrated and subjected to thin-layer chromatography (hexane:ethyl acetate=3:1) to give 51 mg (yield 61%) of (4R)-2,3-epoxy-4-(1-octenyl)-5-(6-methoxycarbonylhexylidene)cyclopentenone.

NMR (CDCl$_3$)δ: 0.7–1.0 (m, 3H), 1.0–1.7 (m, 14H), 1.7–2.5 (m, 7H), 3.7 (3H, s), 3.45 (1H, d, J=3 Hz), 3.7 (1H, d, J=3 Hz), 5.20 (1H, dd, J=16.0, 7.0 Hz), 5.65 (1H, dt, J=16.0, 6.0 Hz), 6.60 (1H, t, J=8.0 Hz), (ii) 16 mg (46 microliters) of (4R)-2,3-epoxy-4-(1-octenyl)-5-(6-methoxylcarbonylhexylidene)cyclopentenone was dissolved in 1 ml of acetone. To the solution was added 0.1 ml of concentrated hydrochloric acid, and then the mixture was stirred for 30 minutes. A saturated aqueous solution of sodium hydrogencarbonate was added, and the mixture was extracted with ethyl acetate. The organic layer was washed with a saturated aqueous solution of sodium chloride and dried over anhydrous magnesium sulfate. The dried product was concentrated and subjected to silica gel column chromatography (silica gel, 5 g; eluent, hexane:ethyl acetate=15:1→6:1) to give 11 mg (yield 65%) of (4S)-2-chloro-4-(1-octenyl)-5-(6-methoxycarbonylhexylidene)-2-cyclopentenone.

IR (liquid film): 1738, 1710, 1657, 1586 cm$^{-1}$.
NMR (CDCl$_3$)δ: 0.84 (brt, 3H, J=4.7 Hz), 1.0–1.8 (m, 14H), 1.8–2.5 (m, 6H), 3.70 (s, 3H), 3.7–4.1 (m, 1H), 5.10 (dd, 1H, J=14.6, 8.0 Hz), 5.50 (dt, 1H, J=14.6, 6.3 Hz), 6.65 (brt, 1H, J=7.3 Hz), 7.13 (brd, 1H, J=3.3 Hz).

EXAMPLE 12

Synthesis of (4R)-2-chloro-4-(1-octenyl)-5-(6-methoxycarbonyl-hexylidene)-2-cyclopentanone (i) To a solution of 600 mg (1.8 mmol) of (4R)-4-(1-octenyl)-5-(6-methoxycarbonylhexylidene)-2-cyclopentenone in 6 ml of methanol was added 0.92 ml (9.0 mmol) of 30% aqueous hydrogen peroxide with ice cooling and stirring, and then 60 microliters (60 micromol) of 1N aqueous sodium hydroxide was added. The mixture was stirred at 0 C. for 45 minutes. A saturated aqueous solution of ammonium chloride was added, and the mixture was extracted with hexane. The organic layer was washed with a saturated sodium chloride, dried over anhydrous magnesium sulfate, filtered, concentrated and subjected to silica gel column chromatography (silica gel, 40 g; eluent, hexane:ethyl acetate=10:1→5:1) to give 491 mg (yield 78%) of (4S)-2,3-epoxy-4-(1-octenyl)-5-(6-methoxycarbonyl-hexylidene)cyclopentenone.

NMR (CDCl$_3$)δ: 0.84 (brt, 3H, J=4.6 Hz), 1.0–1.8 (m, 14H), 1.7–2.5 (m, 6H), 3.3–3.5 (m, 1H), 3.57 (s, 3H), 3.5–3.8 (m, 2H), 5.15 (dd, 1H, J=14.4, 7.0 Hz), 5.47 (dt, 1H, J=14.4, 5.8 Hz), 6.57 (td, 1H, J=7.2, 2.0 Hz).

(ii) To a solution of 450 mg (1.29 mmol) of (4S)-2,3-epoxy-4-(1-octenyl)-5-(6-methoxycarbonylhexylidene)-cyclopentenone in 12 ml of acetone was added 2 ml of concentrated hydrochloric acid at room temperature under stirring. The mixture was stirred for 2 hours. A saturated aqueous solution of sodium hydrogencarbonate was added, and the mixture was concentrated. The product was extracted with ethyl acetate. The organic layer was washed with a saturated aqueous solution of sodium chloride and dried over anhydrous magnesium sulfate. The dried product was filtered, concentrated and subjected to silica gel column chromatography (silica gel, 40 g; eluent, hexane:ethyl acetate = 10:1→5:1) to give 19 mg (yield 4%) of a less polar isomer (Z-form) of (4R)-2-chloro-4-(1-octenyl)-5-(6-methoxycarbonylhexylidene)cyclopentanone and 177 mg (yield 37%) of a more polar isomer (E-form).

Z-form.

NMR (CDCl$_3$)δ: 0.84 (brt, 3H, J=4.8 Hz), 1.0–2.5 (m, 18H), 2.5–3.1 (m, 2H), 3.58 (s. 3H), 3.5–3.9 (m, 1H), 5.08 (dd, 1H, J-14.8, 7.8 Hz), 5.52 (dt, 1H, 14.8, 6.1 Hz), 5.98 (brt, 1H, J=7.6 Hz), 7.07 (d, 1H, 2.4 Hz), E-form.

NMR (CDCl$_3$)δ: 0.84 (brt, 3H, J=4.5 Hz), 1.0–2.5 (m, 20H), 3.58 (s, 3H), 3.7–4.1 (m, 1H), 5.11 (dd, 1H, J=15.2, 8.0 Hz), 5.56 (dt, 1H, J=15.2, 6.2 Hz), 6.62 (brt, 1H, J=7.0 Hz), 7.11 (d, 1H, J=2.8 Hz).

EXAMPLE 13

Synthesis of (4R)-2-chloro-4-(1-octenyl)-5-(6-carboxyhexylidene)-2-cyclopentenone 450 ml of 0.1M phosphate buffer (pH8) was added to a solution of 734 mg (2.0 mmol) of (4R)-2-chloro-4-(1-octenyl)-5-(6-methoxy-carbonylhexylidene)-2-cyclopentenone in 45 ml of acetone, and then 45 ml of an aqueous solution of pig liver esterase was added. The mixture was stirred at 30°–35° C. for 100 hours. 0.1N hydrochloric acid was added to the reaction mixture to adjust its pH to 4, and then the mixture was saturated with ammonium sulfate. It was filtered, and then extracted with ethyl acetate. The organic layer was washed with a saturated aqueous solution of sodium chloride and dried over anhydrous magnesium sulfate. The dried product was filtered, concentrated and subjected to silica gel column chromatography (silica gel, 50 mg; eluent, hexane:acetone:acetic acid = 10:2:0.05→5:2:0.003) to give 480 mg (yield 68%) of (4R)-2-chloro-4-(1-octenyl)-5-(6-carboxyhexylidene)-2-cyclopentenone.

NMR (CDCl$_3$)δ: 0.84 (3H, brt, J=5.6 Hz), 1.0–2.5 (20H, m), 3.7–4.1 (1H, m), 5.07 (1H, dd, J=15.0, 78.0 Hz), 5.60 (1H, dt, J=15.0, 6.0 Hz), 6.64 (1H, brt, J=9.0 Hz), 7.06–7.28 (1H, m), 7.4–8.3 (1H, m).

EXAMPLE 14

Synthesis of 2-chloro-4-(3-hydroxy-1-octenyl)-5-[3-(1-methoxy-carbonylethyloxy)phenylmethylidene]-2-cyclopentenone 0.2 ml of 30% aqueous hydrogen peroxide was added to a solution of 100 mg (0.25 mmol) of 4-(3-hydroxy-1-octenyl)-5-[3-(1-methoxycarbonylethyloxy)-phenylmethylidene]-2-cyclopentenone in 2 ml of methanol under ice cooling and stirring, and then 50 microliters of 1N sodium hydroxide was added. The mixture was stirred at 0° C. for 20 minutes. A saturated aqueous solution of ammonium chloride was added, and the mixture was extracted with hexane. The organic layer was washed with a saturated aqueous solution of sodium chloride and dried over anhydrous sodium sulfate. The dried product was filtered and concentrated to give an oily product. The product was dissolved in 3 ml of acetone, and 0.5 ml of concentrated hydrochloric acid was added. The mixture was stirred for 50 minutes. A saturated aqueous solution of sodium hydrogen carbonate was added, and the mixture was extracted with ethylacetate. The organic layer was washed with a saturated aqueous solution of sodium chloride and dried over anhydrous sodium sulfate. The dried product was filtered, concentrated and subjected to silica gel column chromatography (silica gel, 10 g; eluent, cyclohexane:ethylacetate=4:1) to give 45 mg (yield 41%) of 2-chloro-4-(3-hydroxy-1-octenyl)-5-[3-(1-methoxycarbonylethyloxy)phenylmethylidene]-2-cyclopentenone.

NMR (CDCl$_3$)δ: 0.80 (3H. brt), 0.9–1.4 (8H, m), 1.58 (3H, d, J=6.5 HZ), 2.23 (1H, brs), 3.75 (3H, S), 3.7–4.1 (1H, m), 4.25–4.55 (1H, m), 4.80 (1H, q, J=6.5 HZ), 5.4–5.8 (2H, m), 6.7–7.7 (6H, m).

EXAMPLE 15

Synthesis of 2-chloro-4-(3-hydroxy-3-cyclopentyl-1-propenyl)-5-(6-methoxycarbonyl-2-hexenylidene)-2-cyclopentenone 0.2 ml of 30% aqueous hydrogen peroxide was added to a solution of 65 mg (190 micromol) of 4-(3-hydroxy-3-cyclopentyl-1-propenyl)-5-(6-methoxycarbonyl-2-hexenylidene)-2-cyclopentenone in 2 ml of methanol under ice cooling and stirring, and then 50 microliters of 1N sodium hydroxide was added. The mixture was stirred at 0° C. for 20 minutes. A saturated aqueous solution of ammonium chloride was added, and the mixture was extracted with hexane. The organic layer was washed with a saturated aqueous solution of sodium chloride and dried over anhydrous sodium sulfate. The dried product was filtered and concentrated to give an oily product. The product was dissolved in 3 ml of acetone, and 0.5 ml of concentrated hydrochloric acid was added. The mixture was stirred for one hour. A saturated aqueous solution of sodium hydrogencarbonate was added, and the mixture was extracted with ethylacetate. The organic layer was washed with a saturated aqueous solution of sodium chloride and dried over anhydrous sodium sulfate. The dried product was filtered, concentrated and subjected to silica gel column chromatography (silica gel, 10 g; eluent, cyclohexane:ethylacetate=4:1) to give 27 mg (yield 38%) of 2-chloro-4-(3-hydroxy-3-cyclopentyl-1-propenyl)-5-(6-methoxycarbonyl-2-hexenylidene)-2-cyclopentenone.

NMR (CDCl$_3$)δ: 0.9–2.3 (11H, m), 2.3–2.8 (5H, m), 3.70 (3H, S), 3.45–4.40 (2H, m), 5.5–5.9 (2H, m), 6.5–6.9 (1H, m), 7.3–7.6 (m, 1H).

EXAMPLE 16

Synthesis of 2-chloro-4-(3-hydroxy-5-methyl-1-nonenyl)-5-(6-methoxycarbonyl-5-hexenylidene)-2-cyclopentenone 0.3 ml of 30% aqueous hydrogen peroxide was added to a solution of 160 mg (428 micromol) of 4-(3-hydroxy-5-methyl-1nonenyl)-5-(6-methoxycarbonyl-5-hexenylidene)-2-cyclopentenone in 5 ml of methanol under ice cooling and stirring, and then 60 microliters of 1N sodium hydroxide was added. The mixture was stirred at 0° C. for 20 minutes. A saturated aqueous solution of ammonium chloride was added, and the mixtue was extracted with hexane. The organic layer was washed with a saturated aqueous solution of sodium chloride and dried over anhydrous sodium sulfate. The dried product was filtered and concentrated to give an oily product. The product was dissolved in 3 ml of acetone, and 0.5 ml of concentrated hydrochloric acid was added. The mixture was stirred for 50 minutes. A saturated aqueous solution of sodium hydrogencarbonate was added, and the mixture was extracted with ethylacetate. The organic layer was washed with a saturated aqueous solution of sodium chloride and dried over anhydrous sodium sulfate. The dried product was filtered, concentrated and subjected to silica gel column chromatography (silica gel, 10 g; eluent, cyclohexane:ethylacetate=4:1) to give 82 mg (yield 47%) of 2-chloro-4-(3-hydroxy-5-methyl-1-nonenyl)-5-(6-methoxycarbonyl-5-hexenylidene)-2-cyclopentenone.

NMR (CDCl$_3$)δ: 0.7–1.0 (6H, m), 1.0–1.9 (11H, m), 1.9–2.5 (5H, m), 3.70 (3H, S), 3.8–4.4 (2H, m), 5.1–6.0 (3H, m), 6.70 (1H, brt, J=6.8 HZ), 6.94 (1H, dt, J=16.0, 6.2 HZ), 7.26 (1H, d, J=2.8 HZ).

EXAMPLE 17

Synthesis of 2-chloro-4-(6-methoxycarbonylhexyl)-5-(2-octenylidene)-2-cyclopentenone 0.5 ml of 30% aqueous hydrogen peroxide was added to a solution of 95 mg (286 mmol) of 4-(6-methoxycarbonylhexyl)-5-(2-octenylidene)-2-cyclopentenone in 4 ml of methanol under ice cooling and stirring, and then 0.1 ml of 1N sodium hydroxide was added. The mixture was stirred at 0° C. for 20 minutes. A saturated aqueous solution of ammonium chloride was added, and the mixture was extracted with hexane. The organic layer was washed with a saturated aqueous solution of sodium chloride and dried over anhydrous sodium sulfate. The dried product was filtered and concentrated to give an oily product. The product was dissolved in 3 ml of acetone, and 0.5 ml of concentrated hydrochloric acid was added, the mixture was extracted with ethylacetate. The organic layer was washed with a saturated aqueous solution of sodium chloride and dried over an anhydrous sodium sulfate. The product was filtered, concentrated and subjected to silica gel column chromatography (silica gel, 10 g; eluent, cyclohexane:ethylacetate=10:1) to give 58 mg (yield 55%) of 2-chloro-4-(6-methoxycarbonylhexyl)-5-(2-octenylidene)-2-cyclopentenone.

NMR (CDCl$_3$)δ: 0.83 (3H, brt, J=5.6 HZ), 1.0–2.5 (20H, m), 3.65 (3H, S), 3.4–3.7 (1H, m), 6.1–6.5 (2H, m), 6.8–7.15 (1H, m), 7.3–7.5 (1H, d, J=2.6 HZ).

EXAMPLE 18

Synthesis of 2-chloro-4[(2Z)-6-methoxycarbonyl-2-hexenyl]-5-(2-octenylidene)-2-cyclopentenone 0.5 ml of 30% aqueous hydrogen peroxide was added to a solution of 68 mg (206 micromol) of 4-[(2Z)-6-methoxycarbonyl-2-hexenyl]-5-(2-octenylidene)-2-cyclopentenone in 5 ml of methanol under ice cooling and stirring, and then 50 microliters of 1N sodium hydroxide was added. The mixture was stirred at 0° C. for 20 minutes. A saturated aqueous solution of ammonium chloride was added, and the mixture was extracted with hexane. The organic layer was washed with a saturated aqueous solution of sodium chloride and dried over anhydrous sodium sulfate. The dried product was filtered and concentrated to give an oily product. The product was dissolved in 3 ml of acetone, and 0.5 ml of concentrated hydrochloric acid was added. The mixture was stirred for one hour. A saturated aqueous solution of sodium hydrogencarbonate was added, and the mixture was extracted with ethylacetate. The organic layer was washed with a saturated aqueous solution of sodium chloride and dried over anhydrous sodium sulfate. The dried product was filtered, concentrated and subjected to silica gel column chromatography (silica gel, 10 g; eluent, cyclohexane:ethylacetate=4:1) to give 37 mg (yield 49%) of 2-chloro-4-[(2Z)-6-methoxycarbonyl-2-hexenyl]-5-(2-octenylidene)-2-cyclopentenone.

NMR (CDCl$_3$)δ: 0.86 (3H, brt, J=5.7 HZ), 1.0–2.5 (16H, m), 3.66 (3H, S), 3.5–3.7 (1H, m), 5.3–5.7 (2H, m), 6.1–6.6 (2H, m), 7.0–7.15 (1H, m) 7.3–7.5 (1H, d, J=2.6 HZ).

EXAMPLE 19

Synthesis of 2-chloro-4-(2-octenyl)-5-(6-methoxycarbonylhexylidene)-2-cyclopentenone 0.3 ml of 30% aqueous hydrogen peroxide was added to a solution of 75 mg (226 micromol) of 4-(2-octenyl)-5-(6-methoxycarbonylhexylidene)-2-cyclopentenone in 3 ml of methanol under ice cooling and stirring, and then 70 microliters of 1N sodium hydroxide was added. The mixture was stirred at 0° C. for 20 minutes. A saturated aqueous solution of ammonium chloride was added, and the mixture was extracted with hexane. The organic layer was washed with a saturated aqueous solution of sodium chloride and dried over anhydrous sodium sulfate. The dried product was filtered and concentrated to give an oily product. The product was dissolved in 3 ml of acetone, and 0.5 ml of concentrated hydrochloric acid was added. The mixture was stirred for one hour. A saturated aqueous solution of sodium hydrogen carbonate was added, and the mixture was extracted with ethylacetate. The organic layer was washed with a saturated aqueous solution of sodium chloride and dried over anhydrous sodium sulfate. The dried product was filtered, concentrated and subjected to silica gel column chromatography (silica gel, 10 g; eluent, cyclohexane:ethylacetate=10:1) to give 45 mg (yield 54%) of 2-chloro-4-(2-octenyl)-5-(6-methoxycarbonylhexylidene)-2-cyclopentenone.

NMR (CDCl$_3$)δ: 0.88 (3H, brt, j=5.4 HZ), 1.0–2.70 (20H, m), 3.25–3.7 (1H, m), 3.67 (3H, S), 5.0–5.7 (2H, m), 6.68 (1H, brt, J=7.0 HZ), 7.42 (1H, d, J=2.5 HZ).

REFERENCE EXAMPLE 1

Measurement of the action of inhibiting proliferation of L1210 leukemia cells

L1210 leukemia cells were added to an RPMI medium containing 10% FCS (fetal calf serum), and the concentration of the cells was adjusted to $1 \times 10^5$ cells/ml. Each of the test compounds shown in Table 1 was dissolved in 99.5% ethanol. Prior to use, the final concentration of the ethanol solution was adjusted to less than 0.1%, and it was added to the culture medium. The culture medium was then maintained at 37° C. in a stationary condition for 4 days. After the cultivation, the number of surviving cells was measured by dyeing with trypan blue. As a control, 0.1% ethanol was used. A dose-response curve was plotted from the ratios of proliferation against the control, and $IC_{50}$ was determined.

The results are shown in Table 1.

TABLE 1

| Test Compound | $IC_{50}$ (μg/ml) |
|---|---|
| 2-chloro-4-butyl-5-(6-methoxycarbonyl hexylidene)-2-cyclopentenone (E-form) | 0.1 |
| 2-chloro-4-butyl-5-(6-methoxycarbonyl hexylidene)-2-cyclopentenone (Z-form) | <0.3 |
| 2-bromo-4-butyl-5-(6-methoxycarbonyl hexylidene)-2-cyclopentenone (E-form) | 0.2 |
| 2-bromo-4-butyl-5-(6-methoxycarbonyl hexylidene)-2-cyclopentenone (Z-form) | 0.1 |

REFERENCE EXAMPLE 2

Measurement of the antitumor effect on Ehrich ascites carcinoma $1 \times 10^5$ Ehrlich ascites carcinoma cells were intraperitoneally administered to ICR mice. After the lapse of 24 hours, 30 mg/kg/day or 20 mg/kg/day of 2-chloro-4-butyl-5-(6-carboxyhexylidene)-2-cyclopentenone (E-form) was intraperitoneally administered to the mice for 5 days. The periods of survival of these animals were examined.

In the case where 30 mg/kg/day of 2-chloro-4-butyl-5-(6-carboxyhexylidene)-2-cyclopentenone was administered, the increase of life span (ILS%) increased by 30.7% over the control. In the case of administering 20/mg/kg/day, the increase of life span (ILS%) increased by 40.2%.

REFERENCE EXAMPLE 3

Measurement of the antimicrobial activity against Gram positive and negative bacterium One loopful of cell suspension ($10^8$ cells/ml) was inoculated on heart infusion agar medium containing various levels of a compound of this invention (2-chloro-4-n-butyl-5-(6-carboxyhexylidene)-2-cyclopentenone). The minimum inhibitory concentrations (MIC) was determined by a standard serial twofold dilution method. The results are shown in Table 2.

TABLE 2

| Strains Tested | MIC (μg/ml) |
|---|---|
| G (+) B. subtilis ATCC 6633 | 6.24 |
| G (+) S. aureus MS 353 | 100 |
| G (−) P. aeruginosa IFO 3445 | 100 |
| G (−) P. vulgaris H × 19 | 25 |

REFERENCE EXAMPLE 4

Measurement of inhibitory activities on herpes simplex virus replication

To evaluate the inhibitory effect of 2-chloro-4-(3,7-dimethyl-6-octenyl)-5-(6-carbomethoxyhexylidene)-2-cyclopentenone against herpes simplex virus [HSV] replication in vitro, human embryo lung cells [HELR66] were grown in 6-well Falcon plates in Eagle's minimal essential medium [MEM] supplemented with 5 percent fetal calf serum [CS] and antibiotics.

The test compound was dissolved in absolute ethanol and diluted to the appropriate concentrations with culture medium just before use. The cells were incubated at 37° C. in a humidified atmosphere containing 5 percent $CO_2$ and 95 percent air. Confluent monolayers of the cells were treated with 4 μg/ml of the test compound for 24 hrs. before HSV infection. The test compound pretreated cells were infected with HSV type-1 (strain KOS) or HSV type-2 (strain YS-4) at a m.o.i. of 1. After 1 hr. of incubation at 37° C., the cells were further incubated for 24 hrs. with MEM containing with 2 percent CS, antibiotics and 4 μg/ml the test compound. Control media contained the identical concentration of ethanol. HSV infected HEL-R66 cells were harvested with a rubber policeman 24 hrs. after HSV inoculation and stored at −70° C. Titrations were performed by plaque assays on Vero cells. The results are shown in Table 3.

TABLE 3

Inhibitory effect of the test compound on HSV replication. Each number is the mean of at least three different wells.

| Treatment | Virus yield (pfu/ml) | |
|---|---|---|
| | HSV type-1 (KOS) | HSV type-2 (YS-4) |
| control | $1.4 \times 10^8$ | $1.4 \times 10^8$ |
| test compound (4 μg/ml) | $3.1 \times 10^4$ | $5.4 \times 10^4$ | pfu: plaque-forming units

While the invention has been described in detail and with reference to specific embodiments thereof, it will be apparent to one skilled in the art that various changes and modifications can be made therein without departing from the spirit and scope thereof.

I claim:

1. A 5-alkylidene-2-halo-4-substituted-2-cyclopentenone represented by the following formula (I)-2:

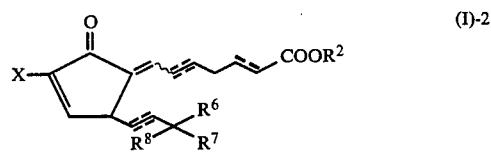

wherein $R^2$ represents a hydrogen atom, an alkyl group having 1 to 10 carbon atoms or one equivalent of a cation, $R^6$ represents a hydrogen atom or a methyl group, $R^7$ represents a hydrogen atom or a substituted or unsubstituted aliphatic hydrocarbon group having 1 to 9 carbon atoms wherein the substituents comprise a halogen atom; —$OR^3$ wherein $R^3$ represents a hydrogen atom, an alkyl group having 1 to 6 carbon atoms which is unsubstituted or substituted by a halogen atom, a carboacyl group having 1 to 7 carbon atoms, or a phenyl group which is unsubstituted or substituted by a halogen atom, an alkyl group having 1 to 4 carbon atoms which is unsubstituted or substituted by a halogen atom, or an alkoxy group having 1 to 4 carbon atoms; a phenyl group which may be substituted by a halogen atom, an alkyl group having 1 to 4 carbon atoms or an alkoxy group having 1 to 4 carbon atoms which may be substituted by a carboacyl group having 1 to 7 carbon atoms; or a cycloalkyl group having 3 to 8 carbon atoms which may be substituted by an alkyl group having 1 to 4 carbon atoms, $R^8$ represents a hydrogen atom, a hydroxyl group or a hydroxyl group protected by a group selected from tri($C_{1-7}$ hydrocarbon)silyl groups and groups forming an acetal linkage with the oxygen atom of the hydroxyl group; the symbol ⟋ represents a single or double bond, and the symbol ⫽ represents a single, double or triple bond.

2. A 5-alkylidene-2-halo-4-substituted-2-cyclopentenone represented by the following general formula (I)-3:

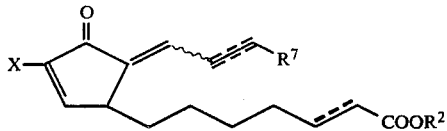

wherein $R^2$ represents a hydrogen atom, an alkyl group having 1 to 10 carbon atoms or one equivalent of a cation, and, $R^7$ represents a hydrogen atom or a substituted or unsubstituted aliphatic hydrocarbon group having 1 to 9 carbon atoms wherein the substituents comprise a halogen atom; —$OR^3$ wherein $R^3$ represents a hydrogen atom, an alkyl group having 1 to 6 carbon atoms which is unsubstituted or substituted by a halogen atom, a carboacyl group having 1 to 7 carbon atoms, or a phenyl group which is unsubstituted or substituted by a halogen atom, an alkyl group having 1 to 4 carbon atoms which is unsubstituted or substituted by a halogen atom, or an alkoxy group having 1 to 4 carbon atoms; a phenyl group which may be substituted by a halogen atom, an alkyl group having 1 to 4 carbon atoms or an alkoxy group having 1 to 4 carbon atoms which may be substituted by a carboacyl group having 1 to 7 carbon atoms; or a cycloalkyl group having 3 to 8 carbon atoms which may be substituted by an alkyl group having 1 to 4 carbon atoms, the symbol ⟋ represents a single or double bond, and the symbol ⫽ represents a single, double or triple bond.

* * * * *